US012619780B2

(12) United States Patent (10) Patent No.: US 12,619,780 B2
Maeda et al. (45) Date of Patent: May 5, 2026

(54) INFORMATION PROCESSING SYSTEM AND INFORMATION PROCESSING METHOD

(71) Applicant: SONY GROUP CORPORATION, Tokyo (JP)

(72) Inventors: Takeshi Maeda, Tokyo (JP); Kana Matsuura, Tokyo (JP); Takuya Nakamura, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 87 days.

(21) Appl. No.: 18/577,722

(22) PCT Filed: Feb. 25, 2022

(86) PCT No.: PCT/JP2022/007794
§ 371 (c)(1),
(2) Date: Jan. 9, 2024

(87) PCT Pub. No.: WO2023/002661
PCT Pub. Date: Jan. 26, 2023

(65) Prior Publication Data
US 2024/0320371 A1 Sep. 26, 2024

(30) Foreign Application Priority Data
Jul. 21, 2021 (JP) ................................. 2021-120291

(51) Int. Cl.
*G06F 21/62* (2013.01)
*G06V 20/52* (2022.01)
(Continued)

(52) U.S. Cl.
CPC .......... *G06F 21/6254* (2013.01); *G06V 20/52* (2022.01); *G06V 40/161* (2022.01); *G16H 30/40* (2018.01)

(58) Field of Classification Search
CPC ................ G06F 21/6254; G06V 20/52; G06V 2201/03; G06V 40/161; G06V 40/171;
(Continued)

(56) References Cited

U.S. PATENT DOCUMENTS

2020/0118677 A1 4/2020 Giataganas
2020/0372180 A1* 11/2020 Venkataraman .... H04L 63/0407
(Continued)

FOREIGN PATENT DOCUMENTS

EP 3188058 A1 7/2017
JP 2002-140685 A 5/2002
(Continued)

OTHER PUBLICATIONS

International Search Report and Written Opinion of PCT Application No. PCT/JP2022/007794, issued on May 17, 2022, 08 pages of ISRWO.

*Primary Examiner* — Olugbenga O Idowu
(74) *Attorney, Agent, or Firm* — CHIP LAW GROUP

(57) ABSTRACT
Provided is an information processing system and an information processing method capable of easily setting or changing an anonymization target to be anonymized according to use of an image captured in a medical facility. Anonymization candidates that can be an anonymization target included in a target image captured in a medical facility are detected, an anonymization target in the target image is determined on the basis of an operation of a user, and an anonymized image obtained by anonymizing an image region of the anonymization target determined by the anonymization target determination unit among the anonymization candidates detected by the image recognition unit is generated for the target image.

15 Claims, 18 Drawing Sheets

(51) Int. Cl.
_G06V 40/16_      (2022.01)
_G16H 30/40_      (2018.01)

(58) Field of Classification Search
CPC .... G06V 40/172; G06V 40/168; G06V 10/44;
        G06V 40/103; G16H 10/60; G16H 30/20;
            G16H 30/40; G06T 2207/30201
See application file for complete search history.

(56)             References Cited

U.S. PATENT DOCUMENTS

| | | | |
|---|---|---|---|
| 2020/0373002 A1* | 11/2020 | Kadambi | ............... G16H 30/40 |
| 2021/0035342 A1 | 2/2021 | Glaser | |
| 2021/0074135 A1 | 3/2021 | Eswara | |

FOREIGN PATENT DOCUMENTS

| | | | |
|---|---|---|---|
| JP | 2006-202130 A | 8/2006 | |
| JP | 2009-123125 A | 6/2009 | |
| JP | 2020-062215 A | 4/2020 | |
| JP | 2021-072606 A | 5/2021 | |
| WO | 2019/244896 A1 | 12/2019 | |

* cited by examiner

INFORMATION PROCESSING SYSTEM AND INFORMATION PROCESSING METHOD

CROSS REFERENCE TO RELATED APPLICATIONS

This application is a U.S. National Phase of International Patent Application No. PCT/JP2022/007794 filed on Feb. 25, 2022, which claims priority benefit of Japanese Patent Application No. JP 2021-120291 filed in the Japan Patent Office on Jul. 21, 2021. Each of the above-referenced applications is hereby incorporated herein by reference in its entirety.

TECHNICAL FIELD

The present technology relates to an information processing system, an information processing method, and a program, and more particularly, to an information processing system, an information processing method, and a program capable of easily setting or changing an anonymization target to be anonymized according to use of an image captured in a medical facility.

BACKGROUND ART

Patent Document 1 discloses a technique for preventing an individual from being identified from a medical image.

CITATION LIST

Patent Document

Patent Document 1: Japanese Patent Application Laid-Open No. 2020-62215

SUMMARY OF THE INVENTION

Problems to be Solved by the Invention

An image captured in a medical facility may be used for various purposes, and it is desirable to easily set and change an anonymization target to be anonymized in the image according to the purpose.

The present technology has been made in view of such a situation, and makes it possible to easily set or change an anonymization target to be anonymized according to the use of an image captured in a medical facility.

Solutions to Problems

An information processing system or a program of the present technology is an information processing system including: an image recognition unit that detects anonymization candidates that can be an anonymization target included in a target image captured in a medical facility; an anonymization target determination unit that determines an anonymization target in the target image on the basis of an operation of a user; and an image processing unit that generates, for the target image, an anonymized image obtained by anonymizing an image region of the anonymization target determined by the anonymization target determination unit among the anonymization candidates detected by the image recognition unit, or a program for causing a computer to function as such an information processing system.

An information processing method of the present technology is an information processing method in an information processing system including: an image recognition unit; an anonymization target determination unit; and an image processing unit, the information processing method including: detecting, by the image recognition unit, anonymization candidates that can be an anonymization target included in a target image captured in a medical facility; determining, by the anonymization target determination unit, an anonymization target in the target image on the basis of an operation of a user; and for the target image, generating, by the image processing unit, an anonymized image obtained by anonymizing an image region of the anonymization target determined by the anonymization target determination unit among the anonymization candidates detected by the image recognition unit.

In the information processing system, the information processing method, and the program of the present technology, anonymization candidates that can be an anonymization target included in a target image captured in a medical facility are detected, an anonymization target in the target image is determined on the basis of an operation of a user, and an anonymized image obtained by anonymizing an image region of the anonymization target determined by the anonymization target determination unit among the anonymization candidates detected by the image recognition unit is generated for the target image.

BRIEF DESCRIPTION OF DRAWINGS

FIG. 3 is a diagram illustrating a result of person information detection processing in a data processing device.

FIG. 7 is a block diagram illustrating a specific configuration of the information processing system in FIG. 1.

FIG. 10 is an explanatory diagram in a case of three-dimensionally detecting a posture of a person included in an image of a camera.

FIG. 12 is a diagram for explaining additional anonymization processing.

FIG. 16 is a diagram for explaining additional anonymization processing.

FIG. 17 is a block diagram illustrating a configuration example of hardware of a computer that executes a series of processing by a program.

FIG. 18 is a diagram schematically illustrating an overall configuration of an operating room system.

MODE FOR CARRYING OUT THE INVENTION

Hereinafter, an embodiment of the present technology will be described with reference to the drawings.

<Embodiment of Information Processing System>

Figure 1:
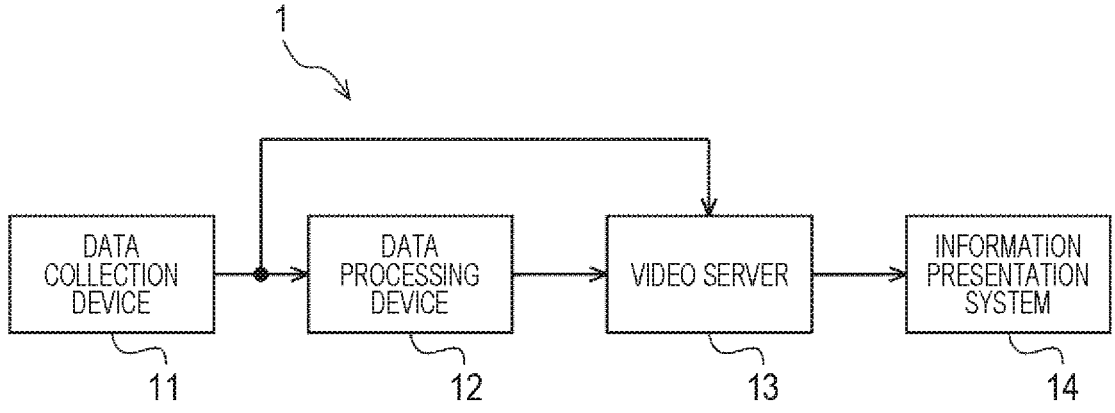
FIG. 1 is a block diagram illustrating a configuration example of an information processing system to which the present technology is applied.

FIG. 1 is a block diagram illustrating a configuration example of an information processing system to which the present technology is applied.

In FIG. 1, an information processing system 1 includes a data collection device 11, a data processing device 12, a video server 13, and an information presentation system 14.

The data collection device 11 collects videos of various places in a facility by one or a plurality of cameras installed in an operating room, a diagnosis room, or the like of a medical facility such as a hospital, and supplies the videos to the data processing device 12 and the video server 13 by communication of a predetermined standard or the like. Note that the camera of the data collection device 11 may be a camera used as a medical device such as an endoscope camera in addition to a ceiling camera provided on the ceiling of an operating room to image the hands of an operator, a surgical field camera provided on the ceiling of the operating room to image the state of the entire operating room, and the like.

The data processing device 12 executes person information detection processing and instrument appearance information detection processing to be described later on the videos collected by the data collection device 11, and detects information (identification information (role or the like), an image region, or the like) of candidates (anonymization candidates) regarding an object to be anonymized (anonymization target) of a person, an instrument, or the like included in the videos. The data processing device 12 supplies information (anonymization candidate information) regarding the detected anonymization candidates to the video server 13 by predetermined standard communication or the like. Note that the data processing device 12 and the video server 13 may be an integrated device.

The video server 13 determines an anonymization target to be actually anonymized from among the anonymization candidates on the basis of the anonymization candidate information from the data processing device 12. When the anonymization target is determined, the video server 13 performs anonymization processing on an image region to be anonymized with respect to the video from the data collection device 11, and generates a video (anonymized video) subjected to the anonymization processing. The video server 13 saves (stores) the anonymized video, and supplies the anonymized video to the information presentation system 14 by communication of a predetermined standard or the like.

The information presentation system 14 outputs the anonymized video from the video server 13 to an output device such as a monitor (also referred to as a display) or a printer.

<Outline of Processing of Information Processing System 1>

FIGS. 2 to 5 are diagrams for explaining an outline of a series of processing in the information processing system 1.

Figure 2:
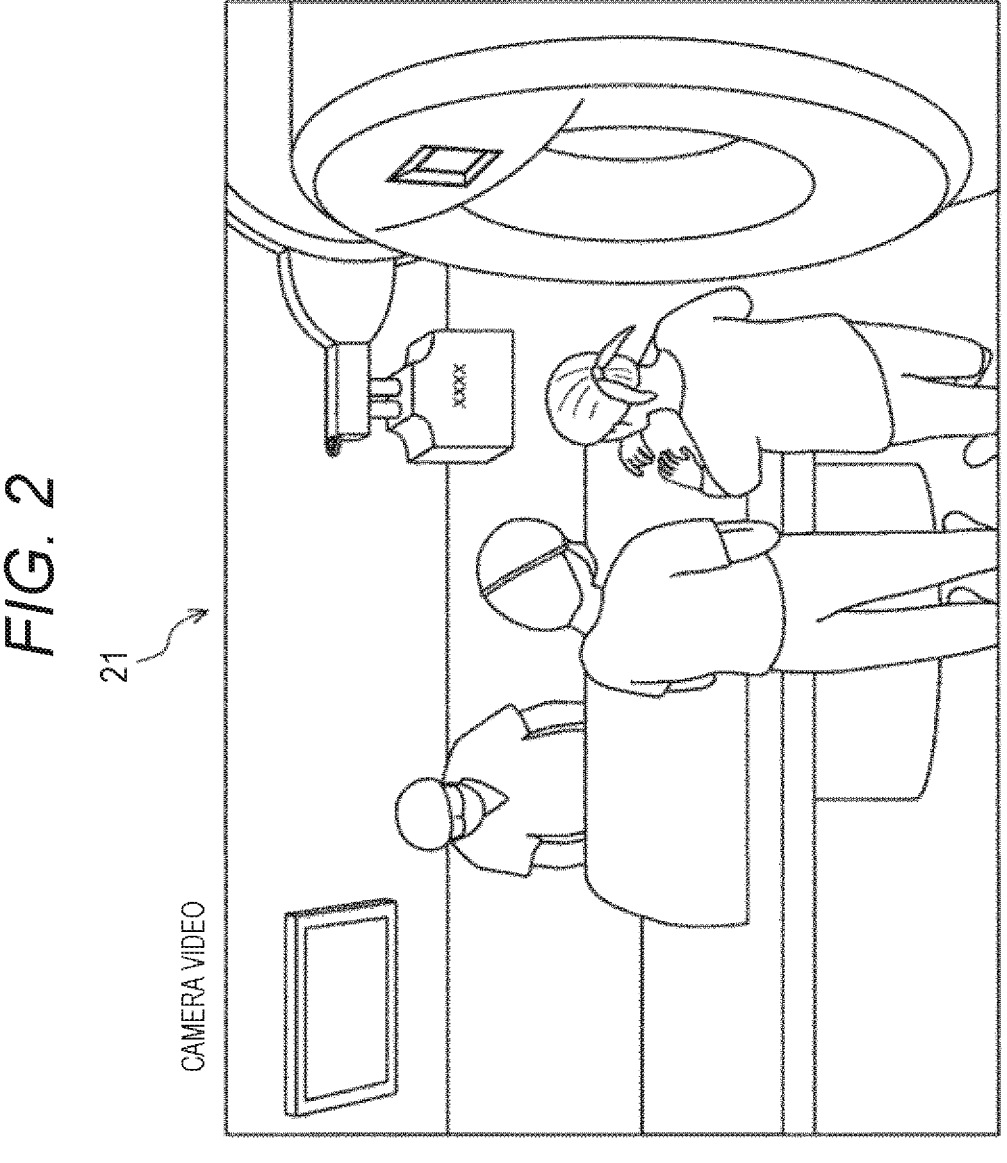
FIG. 2 is a diagram exemplifying videos collected by a data collection device.

FIG. 2 is a diagram illustrating videos (video data) collected by the data collection device 11.

For example, the data collection device 11 captures an image of an operation state with a camera installed in an operating room, and acquires a video 21 as illustrated in FIG. 2. The video is, for example, a moving image including a group of the images (still images) continuously captured at predetermined time intervals. However, the video may be a still image. In a case where the video 21 is represented on the drawing as illustrated in FIG. 2, when the video 21 is a moving image, the video is represented by one frame image among still images (frame images) constituting the video 21. In the information processing system 1 of FIG. 1, it is assumed that the data collection device 11 acquires a plurality of videos by a plurality of cameras installed in various places, but the video 21 of FIG. 2 is mainly used in the description of the processing on the videos.

Figure 3:
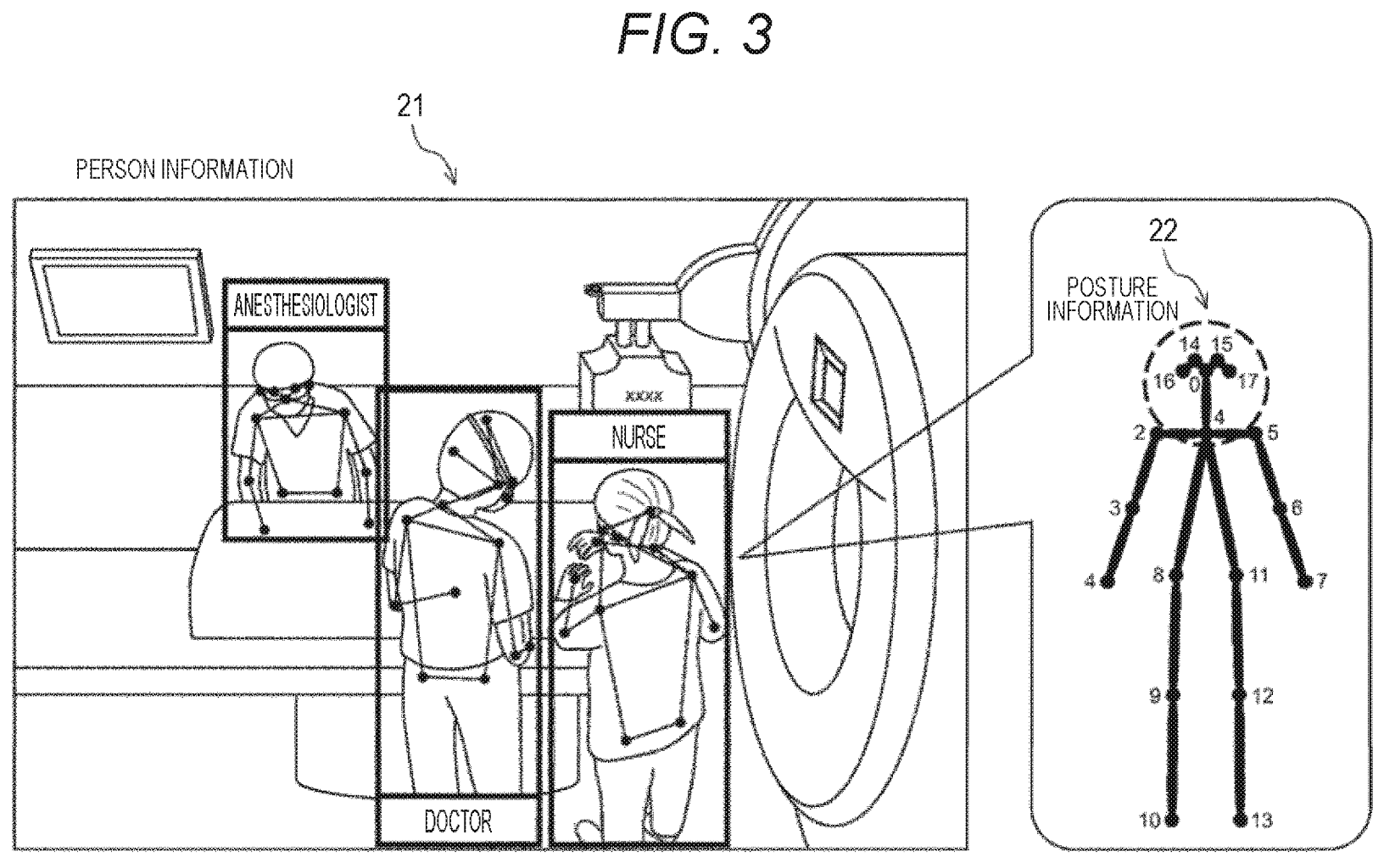

FIG. 3 illustrates a result of the person information detection processing in the data processing device 12. As illustrated in FIG. 3, the data processing device 12 detects persons (all persons) to be anonymization candidates included in the videos collected by the data collection device 11, and estimates a role of the detected person. In the person information detection processing, a skeleton of a person is detected on the basis of detection of a feature portion (joint portion or the like) of the person, and a posture is detected on the basis of the detected skeleton. Note that the detection of the skeleton and the posture of the person may be performed by any method such as a posture/skeleton detection algorithm such as OpenPose. As a result, an image region of the person, a position of the person, an orientation of the body, a position of the hand, and the like in the video 21 are specified.

Furthermore, the role of the person is estimated using a determination database prepared in advance from the position and posture of the person, appearance information such as clothes of the person, the motion of the person, and the like. The role of the person may be estimated by being subdivided into, for example, a surgeon, an assistant, a direct assistant (who takes out an instrument), an indirect assistant (who goes around outside), an anesthesiologist, a perianesthesia nurse, a clinical engineer, an operating room staff (who carries in and out), a contractor (cleaning, disinfection, assistance, and the like), and the like, but in the present specification, the estimated role is assumed to be any one of a doctor, a nurse, an anesthesiologist, and a staff.

Figure 4:
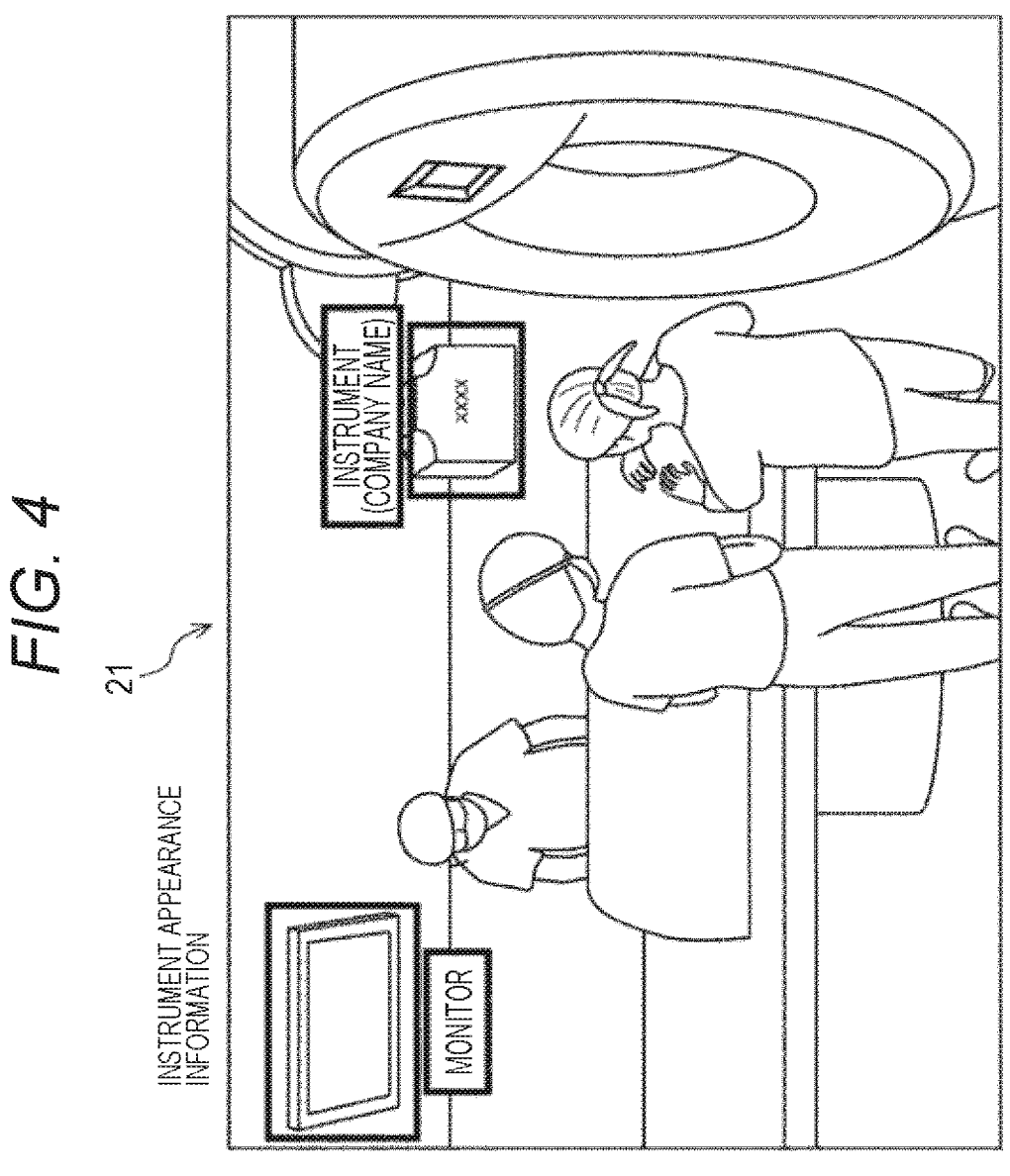
FIG. 4 is a diagram illustrating a result of instrument appearance information detection processing in the data processing device.

FIG. 4 illustrates a result of the instrument appearance information detection processing in the data processing device 12. The data collection device 11 detects an instrument (including a case of a part of the instrument) to be anonymization candidates for the video collected by the data collection device 11 as illustrated in FIG. 4. The instrument to be the anonymization candidates include a monitor (display) and a predetermined instrument. Since there is a possibility that, for example, biological information indicating a condition of a patient in an operating room, an operative field video for confirming progress of an operation, patient information (information leading to identification of an individual), and the like are displayed on a display, the display becomes an anonymization candidate. The instrument to be the anonymization candidates includes an instrument (whole or a written portion of instrument information) in which instrument information such as a company name (logo) and an instrument name is written (printed). The instrument serving as the anonymization candidates is not limited to a medical instrument, and may include a name plate of a surgical staff presented on a wall surface or the like, and a portion in which textual information is written. However, the anonymization candidates are not limited thereto.

Figure 5:
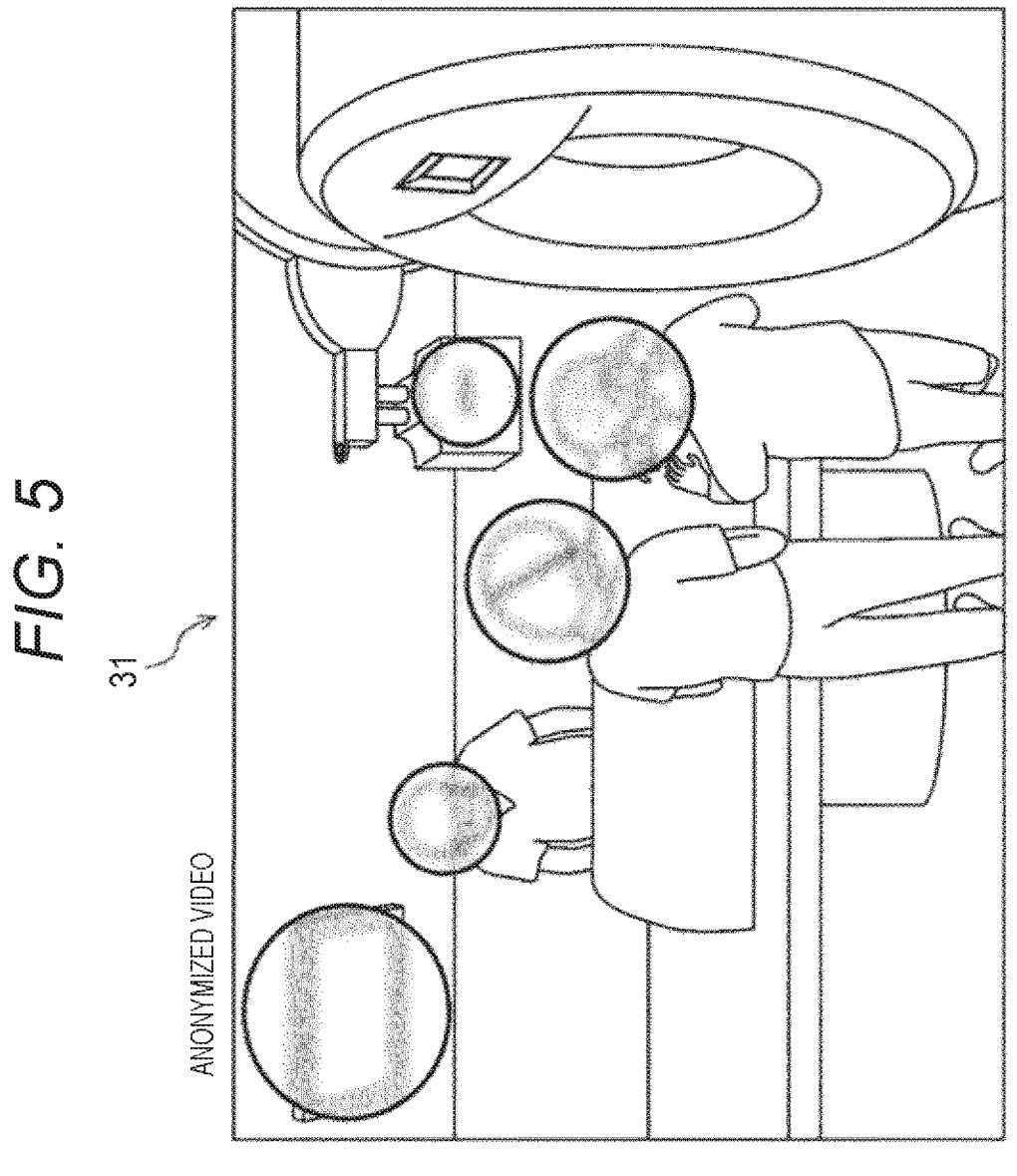
FIG. 5 is a diagram exemplifying an anonymized video generated by anonymization processing in a video server.

FIG. 5 is a diagram exemplifying an anonymized video generated by anonymization processing in the video server 13 and presented by the information presentation system 14. The video server 13 performs, on the video collected by the data collection device 11, anonymization processing such as blurring or mosaic as illustrated in FIG. 5 on an image region of the anonymization target selected on the basis of a user operation among the anonymization candidates detected by the data processing device 12, and generates an anonymized video. An anonymized video 31 in FIG. 5 represents an anonymized video obtained by anonymizing the video 21 in FIG. 2. The anonymized video generated as illustrated in FIG. 5 is stored in the video server 13, transmitted to the information presentation system 14, and output to an output device such as a monitor in the information presentation system 14.

<Procedure Example of Anonymized Video Generation Process in Data Processing Device 12 and Video Server 13>

Figure 6:
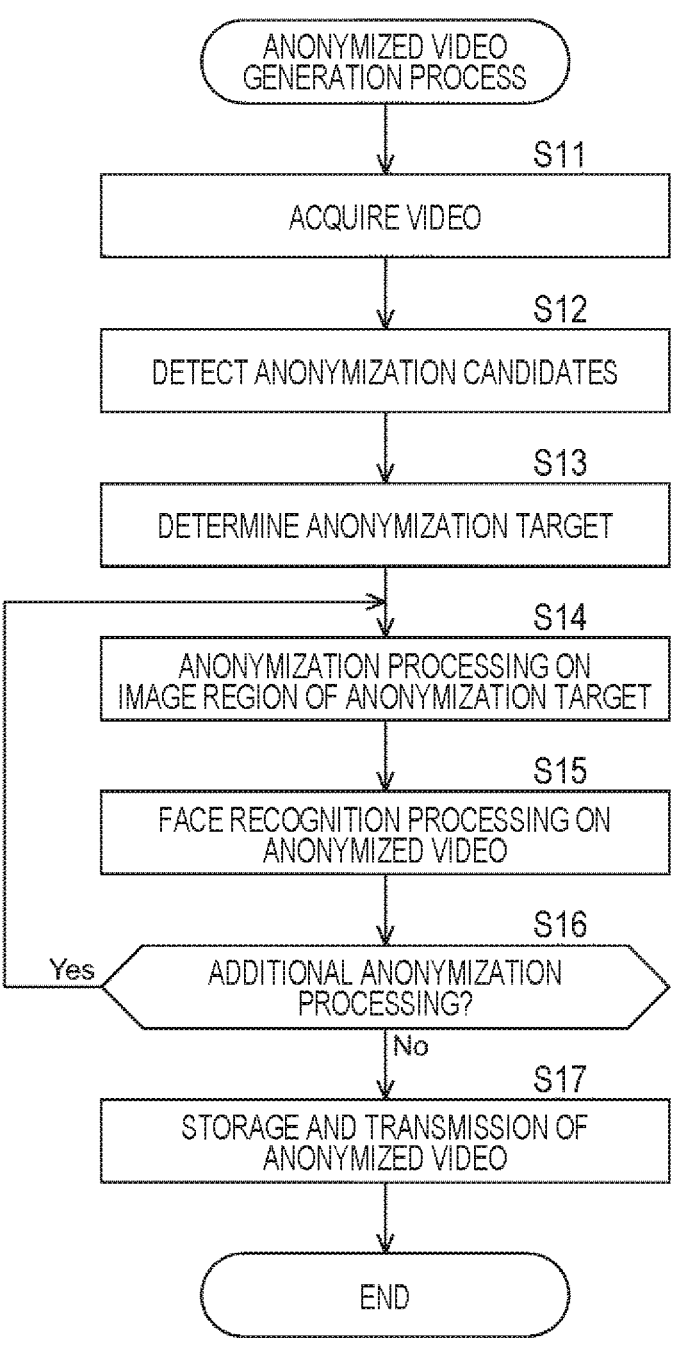
FIG. 6 is a flowchart illustrating a procedure example of an anonymized video generation process performed by the data processing device and the video server.

FIG. 6 is a flowchart illustrating a procedure example of an anonymized video generation process performed by the data processing device 12 and the video server 13.

In step S11, the data processing device 12 acquires a video to be anonymized from the data collection device 11. The process proceeds from step S11 to step S12. In step S12, the data processing device 12 detects anonymization candidates included in the video acquired in step S11.

The process proceeds from step S12 to step S13. In step S13, the video server 13 determines an anonymization target to be anonymized among the anonymization candidates detected in step S12 on the basis of selection (designation) of the user. The process proceeds from step S13 to step S14. In step S14, the video server 13 executes anonymization processing on an image region of the anonymization target determined in step S13, and generates an anonymized video obtained by anonymizing (blurring or abstracting) an image to be anonymized. The process proceeds from step S14 to step S15. In step S15, the video server 13 performs face recognition processing on the anonymized video generated in step S14, and detects an image region (face image) recognized as a face. The process proceeds from step S15 to step S16. In step S16, the user checks the face image detected in step S15, and determines whether or not additional anonymization processing is necessary.

In a case where it is determined in step S16 that the additional anonymization processing is necessary, the process returns to step S14, and steps S14 to S16 are repeated. At that time, in step S14, the video server 13 executes the additional anonymization processing only on an image region selected by the user among the image regions of the face image detected in step S15.

In a case where it is determined in step S16 that the additional anonymization processing is unnecessary, the process proceeds to step S17, and in step S17, the video server 13 stores the anonymized video generated by executing the anonymization processing last in step S14, and transmits the anonymized video to the information presentation system 14. Note that, in step S12, before the anonymization candidates included in the video acquired in step S11 are detected, the anonymization candidates to be an anonymization target may be determined among the anonymization candidates (anonymization candidates to be an anonymization target) that can be detected in step S12 on the basis of the designation of the user. In this case, in step S12, only the anonymization candidates determined as the anonymization target may be detected from the video.

According to this, in a case where anonymization candidates that can be an anonymization target is included in a video obtained by capturing an image of a medical site, only the anonymization candidates selected by the user among the anonymization candidates can be determined as an anonymization target. An anonymized video in which only an image region of an anonymization target selected by the user is anonymized (blurred) can be generated with respect to the video obtained by capturing an image of the medical site, and can be supplied to the information presentation system 14. Therefore, only appropriate anonymization candidates can be anonymized according to the situation in which the video is presented. For example, videos obtained by capturing an image of a state of surgery or diagnosis are increasingly used from an educational viewpoint or the like. Work and a workflow in an operating room are complicated, and there are problems such as inefficient operations. Therefore, in order to solve the problems, it is desired to effectively utilize videos such as analyzing videos obtained by capturing an image of a medical site and rotating a PDCA cycle, and it is desired to share videos among various types of jobs. As a specific example, a video obtained by capturing an image of a medical site may be presented in the following situation. As a first situation, there is a situation in which a terminal used by a doctor who has performed surgery and a terminal used by a patient who has undergone surgery are connected by communication, and at the time of online diagnosis in which the doctor who has performed surgery online explains surgery to the patient, a video obtained by capturing an image of a state of the surgery is presented in the explanation. As a second situation, there is a situation in which a video obtained by capturing an image of a state of diagnosing a patient or a state of surgery is presented at a medical office conference in which scheduled surgery or surgery after being performed is explained or discussed. As a third situation, there is a situation in which a video obtained by capturing an image of a state of surgery, diagnosis, or the like is presented at the time of a study meeting, a lecture, or the like in a conference room or an auditorium where a large number of audiences gather.

In the first situation, it is conceivable to present an anonymized video obtained by anonymizing persons other than the patient and the doctor who performs explanation through online diagnosis among persons appearing in the video. As a result, the patient who is receiving the explanation by the online diagnosis can recognize that the patient shown in the video is himself/herself, and the doctor who is giving the explanation by the online diagnosis is the same person as the doctor shown in the video.

In the second situation, it is not necessary to anonymize the doctor among the persons appearing in the video, and it is conceivable to present an anonymized video obtained by anonymizing persons other than the doctor.

In the third situation, it is conceivable to anonymize all persons appearing in the video or to present an anonymized video obtained by anonymizing persons other than the doctor giving a lecture or the like.

Since the anonymization target that needs to be anonymized differs depending on the situation in which the video is provided as described above, it is desirable to be able to easily select (designate) the anonymization target according to the situation in which the video is presented (use of the video) instead of uniformly anonymizing a person or an instrument appearing in the video as in the conventional case. The video may include not only the appearance of a patient and a medical staff but also a name and related textual information, and it is desired to anonymize these pieces of information from the viewpoint of privacy.

In the prior art document (Patent Document 1), there is no anonymization means to other occupations such as operating room staffs other than a patient, and privacy measures are insufficient when utilizing videos from the viewpoint of improving the workflow of surgery and extracting problems. Furthermore, it is also difficult to select an anonymization target according to a presentation situation (use) of a video. According to the present technology, it is possible to satisfy such a demand, and generate and present an appropriate anonymized video according to a situation.

<Specific Configuration of Information Processing System 1>

Figure 7:
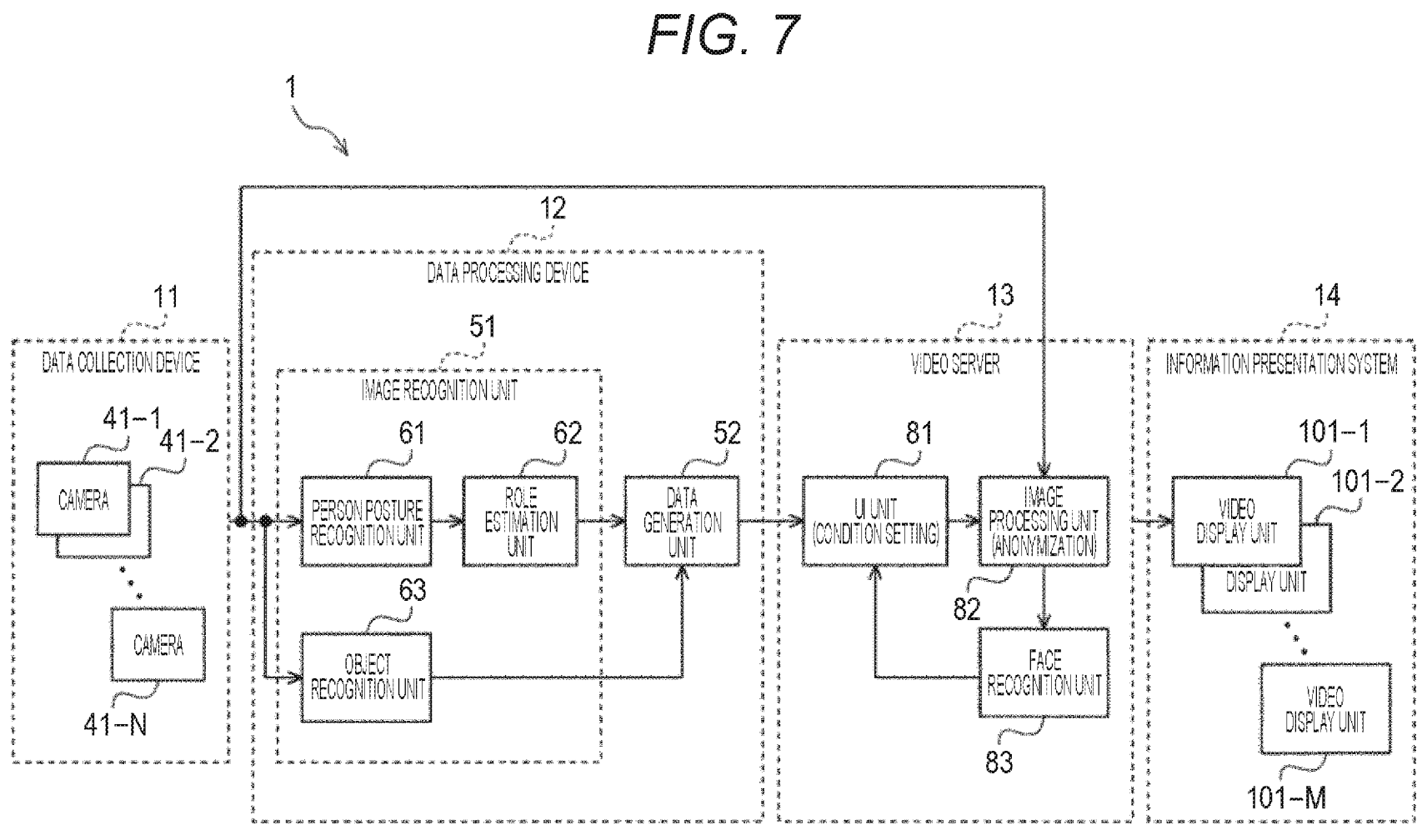

FIG. 7 is a block diagram illustrating a specific configuration of the information processing system 1 of FIG. 1. The data collection device 11 includes one or a plurality of cameras 41-1 to 41-N (N is a positive integer). Each of the cameras 41-1 to 41-N can be installed in various places such as an operating room and a diagnosis room in a medical facility such as a hospital. The videos captured by the cameras 41-1 to 41-N are supplied to the data processing device 12 and the video server 13. Note that, in the following description, it is assumed that one unspecified camera among the cameras 41-1 to 41-N is represented by a camera 41-$n$, and processing on the video obtained by the camera 41-$n$ can be performed on each video obtained by each of all the cameras 41-1 to 41-N.

The data processing device 12 includes an image recognition unit 51 and a data generation unit 52. The image recognition unit 51 performs image recognition processing on the video of the camera 41-$n$ from the data collection device 11, and detects information regarding anonymization candidates included in the video. Specifically, the image recognition processing is person information detection processing and instrument appearance information detection processing, and the anonymization candidates are a person, a monitor (display), and an instrument (object) on which identification information such as instrument information is written. The image recognition unit 51 supplies a detection result of the video of the camera 41-$n$ to the data generation unit 52.

The data generation unit 52 generates data (anonymization candidate information) regarding the anonymization candidates included in the video of the camera 41-$n$ according to a predetermined format on the basis of the result detected by the image recognition unit 51, and supplies the data to the video server 13.

Here, the image recognition unit 51 includes a person posture recognition unit 61, a role estimation unit 62, and an object recognition unit 63. The person posture recognition unit 61 and the role estimation unit 62 execute the person information detection processing described above.

The person posture recognition unit 61 detects the skeleton of the person included in the video of the camera 41-$n$, and recognizes the posture of the person on the basis of the detected skeleton. As a result, an image region of the person, a position of the person, an orientation of the body, a position of the hand, and the like in the video 21 are specified.

The role estimation unit 62 estimates the role (doctor, nurse, anesthesiologist, or staff) of the person detected by the person posture recognition unit 61. The role of the detected person is estimated using a determination database prepared in advance from the position and posture of the person, appearance information such as clothes of the person, the motion of the person, and the like.

The object recognition unit 63 performs the instrument appearance information detection processing described above. The object recognition unit 63 detects, other than a person, an object (instrument) to be anonymization candidates included in the video of the camera 41-$n$. The instrument to be the anonymization candidates is an instrument (portion) on which identification information such as a monitor or instrument information is written.

The results detected by the person posture recognition unit 61, the role estimation unit 62, and the object recognition unit 63 are supplied to the data generation unit 52.

The video server 13 includes a UI unit 81 (anonymization target determination unit), an image processing unit 82, and a face recognition unit 83. The video server 13 saves (stores) the video of the camera 41-$n$ in a storage unit (not illustrated), and the UI unit 81, the image processing unit 82, and the face recognition unit 83 can appropriately acquire all of the video of the camera 41-$n$ or an image of a predetermined frame.

The UI unit 81 controls a UI image to be displayed on a display (screen) that is a display device (not illustrated) on the basis of information (described later) from the face recognition unit 83 and anonymization candidate information from the data generation unit 52 of the data processing device 12. The UI image includes an input image and the like for the user to select (designate) an anonymization target to be actually anonymized from among the anonymization candidates detected by the data processing device 12 for the video of the camera 41-$n$. The UI unit 81 generates a UI image, displays the UI image on a display that is a display device (not illustrated), and determines an anonymization target or the like according to a user's operation from an input device (operation unit) (not illustrated). The information such as the anonymization target determined by the UI unit 81 and the image region thereof is supplied to the image processing unit 82. Note that details of the UI image will be described later.

The image processing unit 82 generates an anonymized video on the basis of the video of the camera 41-$n$ and the information from the UI unit 81. The anonymized video is a video obtained by performing anonymization processing on an image region of the anonymization target included in the video of the camera 41-$n$. The anonymization processing refers to, for example, processing of blurring (abstracting) the image region of the anonymization target by processing such as blurring or mosaic. The anonymization processing may be processing other than blurring or mosaic, and may be any processing of blurring (abstracting) the image region of the anonymization target. The image processing unit 82 supplies the generated anonymized video to the face recognition unit 83 and stores the anonymized video in a storage unit (not illustrated).

The face recognition unit 83 executes face recognition processing on the anonymized video from the image processing unit 82, and recognizes a face included in the anonymized video. The face recognition unit 83 supplies to the UI unit 81 information (image capturing time or the like) for specifying a frame in which a face is recognized in the anonymized video and an image region of the face recognized in the frame.

Note that, in the image region of the face recognized by the face recognition unit 83, additional anonymization processing is performed by the image processing unit 82 according to the selection of the user in the UI unit 81. The anonymized video generated by the image processing unit 82 and stored in the storage unit is an anonymized video reflecting the additional anonymization processing. The anonymized video stored in the storage unit is supplied to the information presentation system 14.

The information presentation system 14 includes one or a plurality of video display units 101-1 to 101-M (M is a positive integer). Each of the video display units 101-1 to 101-M can be disposed in a medical facility where the camera 41-n is installed or in an arbitrary place other than the medical facility. Each of the video display units 101-1 to 101-M includes a display device (display), and displays the anonymized video supplied from the video server 13.

<Configuration Example of Person Posture Recognition Unit 61>

When detecting the posture of the person included in the video of the camera 41-n in the person posture recognition unit 61 of the data processing device 12, in a case where there is a plurality of cameras including a common space with the camera 41-n in an image capturing range, the postures of the person detected from the videos of the cameras may be integrated to three-dimensionally detect the posture of the person.

Figure 8:
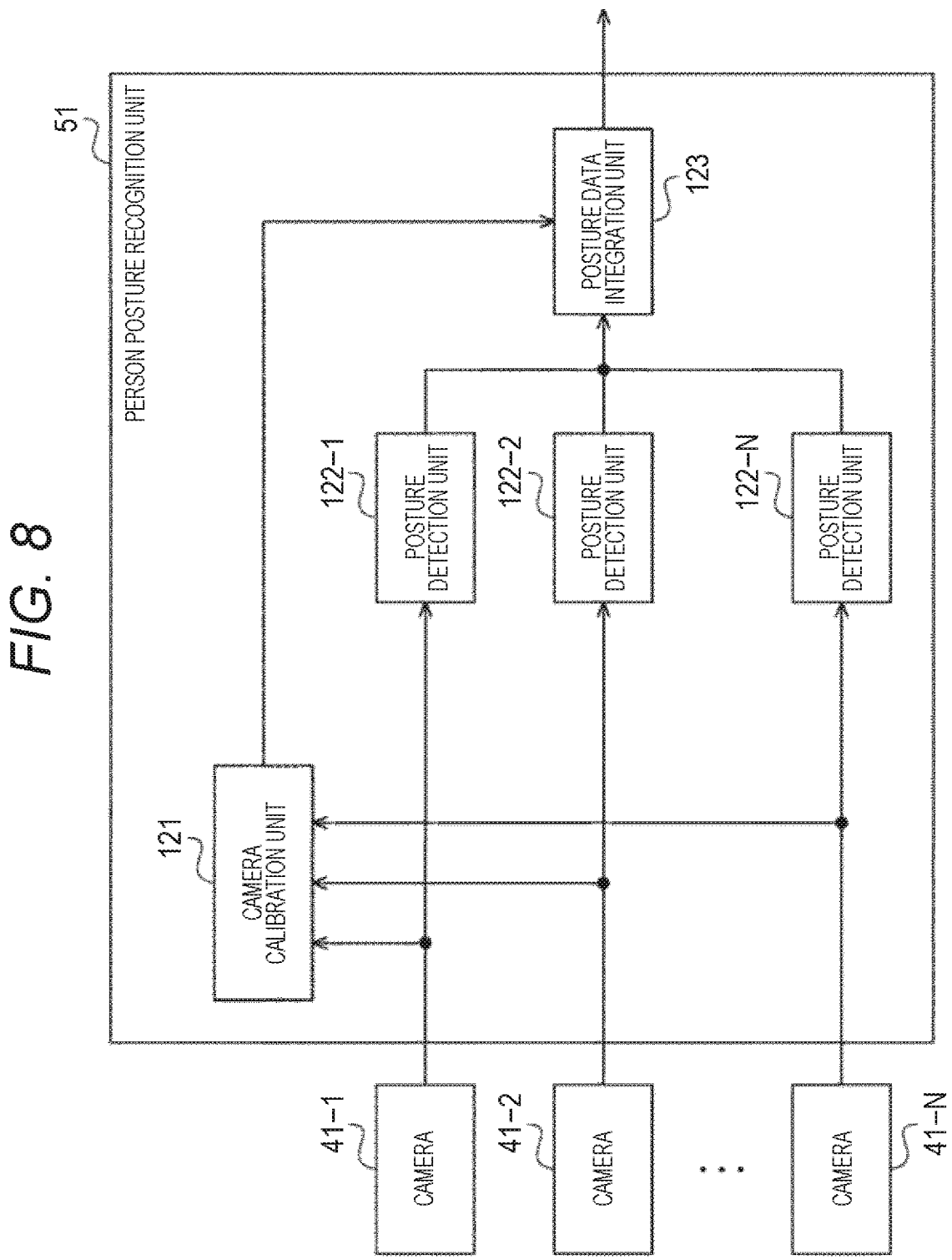
FIG. 8 is a block diagram illustrating a configuration example of a person posture recognition unit in a case where a posture of a person is three-dimensionally detected.

FIG. 8 is a block diagram illustrating a configuration example of the person posture recognition unit 61 in a case where the posture of the person is three-dimensionally detected. In FIG. 8, the person posture recognition unit 61 includes a camera calibration unit 121, posture detection units 122-1 to 122-N, and a posture data integration unit 123.

The camera calibration unit 121 calculates relative positions of the cameras among the cameras 41-1 to 41-N of the data collection device 11 on the basis of a known video (calibration video) acquired in advance from a camera including the same space as an image capturing range, and supplies a result thereof to the posture data integration unit 123.

Figure 9:
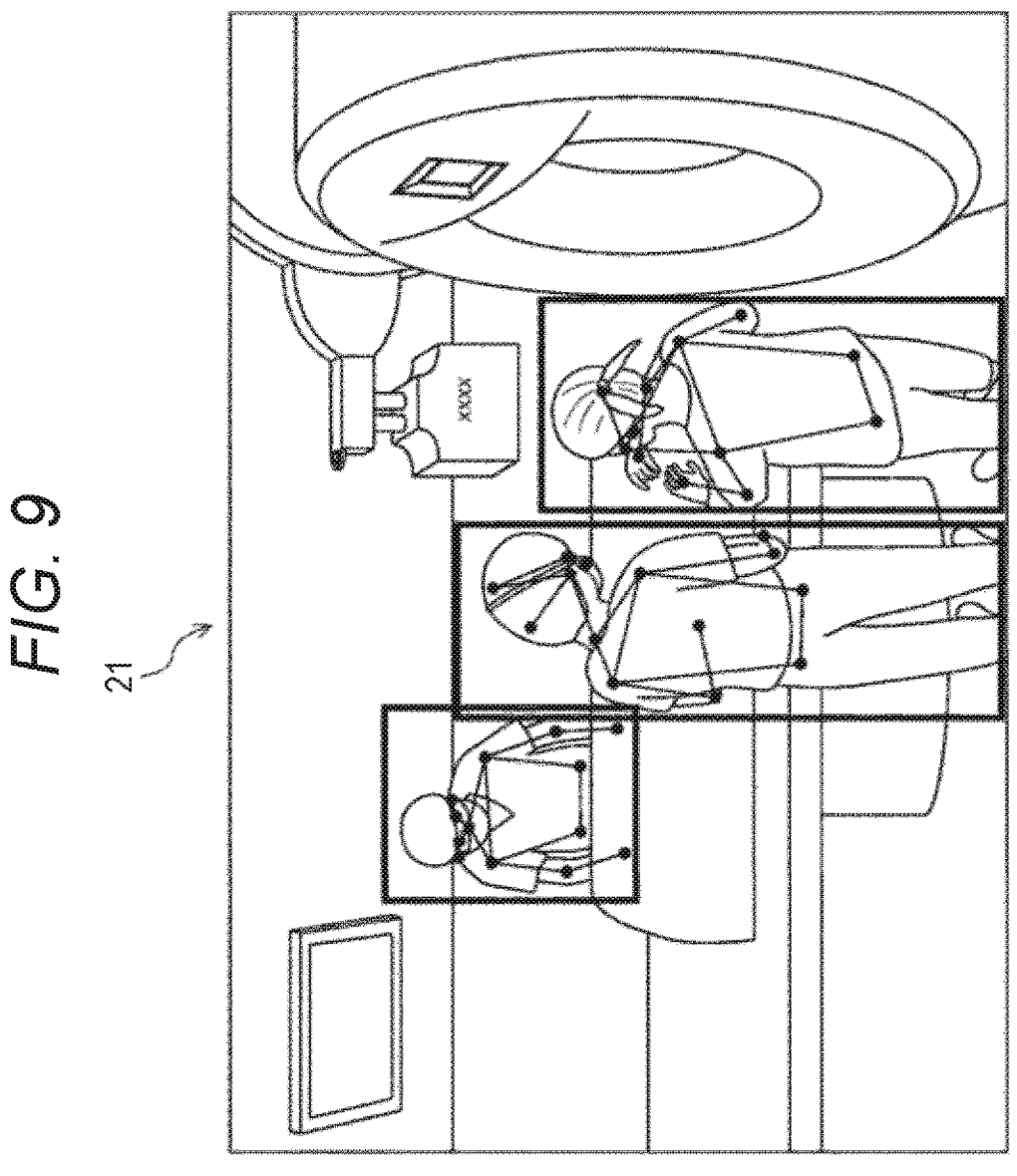
FIG. 9 is an explanatory diagram in a case where a posture of a person included in an image is detected by a skeleton.

The posture detection units 122-1 to 122-N detect, with respect to the videos of the cameras 41-1 to 41-N, the postures of the person included in the videos by the skeleton as illustrated in FIG. 9, and supply the results to the posture data integration unit 123 as posture information.

Figure 10:
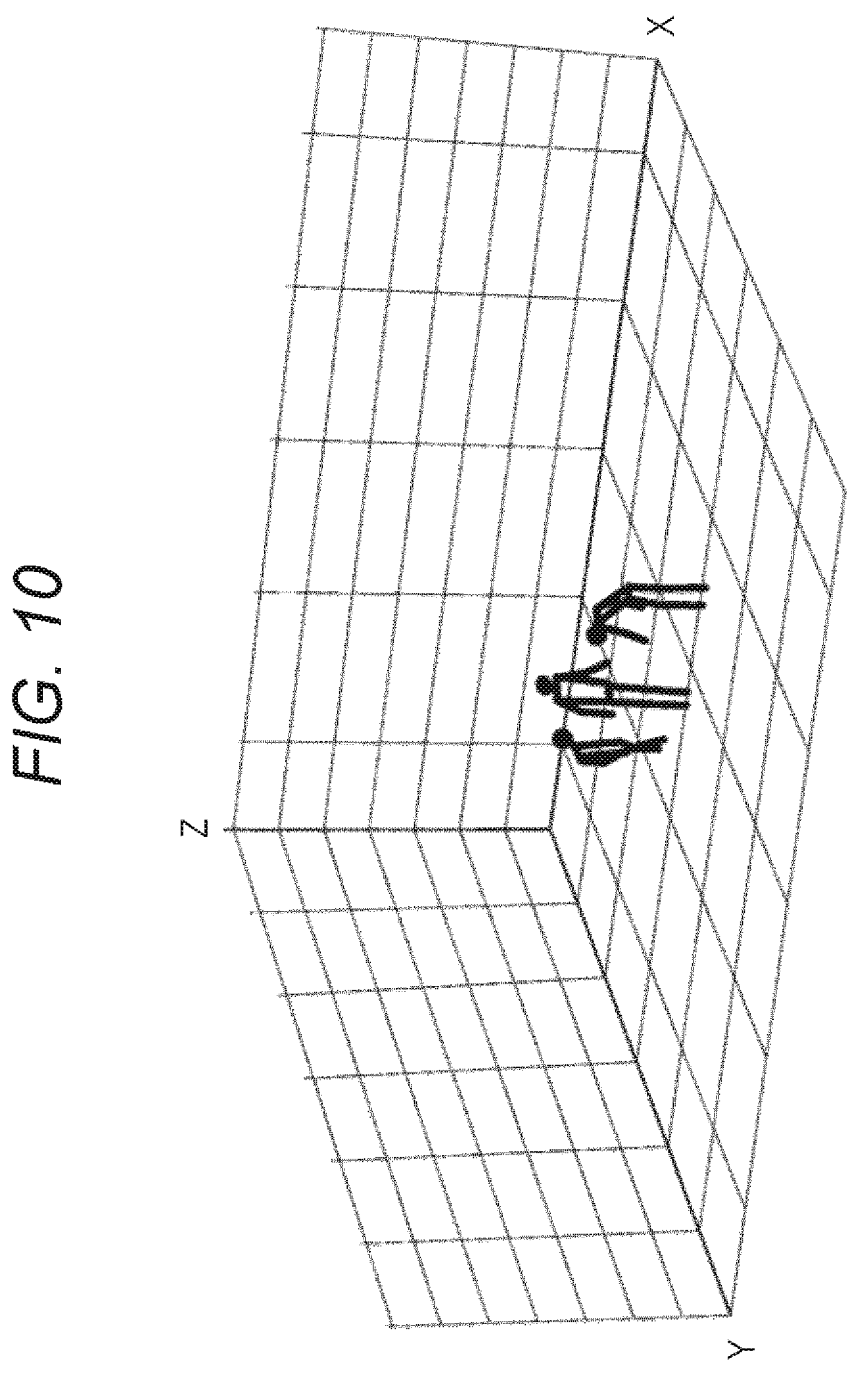

The posture data integration unit 123 extracts the postures of the person included in the videos of the cameras including the same space as the predetermined camera 41-n as the image capturing range from the posture information supplied from the posture detection units 122-1 to 122-N. Note that the postures of the person are extracted for each frame at the same image capturing time of each video. The posture data integration unit 123 integrates the postures of the same person among the extracted postures of the person for each frame, and three-dimensionally detects the posture of the person included in the video of the camera 41-n as illustrated in FIG. 10 using the information of the relative positions of the cameras from the camera calibration unit 121.

<First Embodiment of UI Image>

Figure 11:
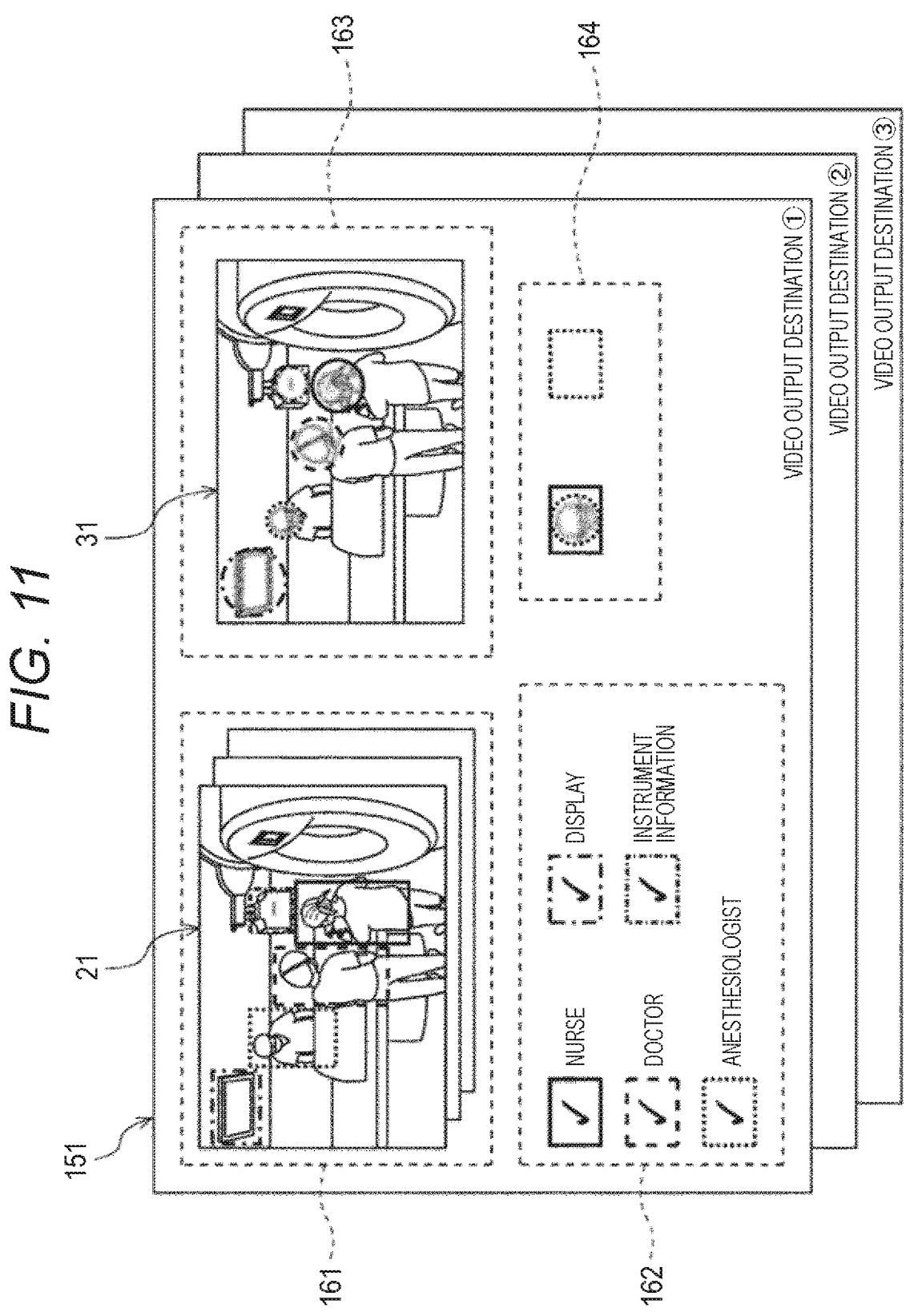
FIG. 11 is a diagram illustrating a configuration example of a first embodiment of a UI image.

FIG. 11 is a diagram illustrating a configuration example of a first embodiment of a UI image generated by the UI unit 81 of the video server 13.

In FIG. 11, a UI image 151 according to the first embodiment represents an image generated by the UI unit 81 and displayed on a display (screen) that is a display device (not illustrated) of the video server 13. It is assumed that a pointing device such as a mouse is used as an input device (not illustrated) that inputs a user's operation. However, the input device is not limited to the pointing device, and may be a keyboard or the like.

The UI image 151 includes an anonymization candidate display unit 161, an anonymization selection unit 162, an anonymization result display unit 163, and a face detection unit 164. Note that each of the anonymization candidate display unit 161, the anonymization selection unit 162, the anonymization result display unit 163, and the face detection unit 164 is not limited to a case of being simultaneously displayed as one screen image as the UI image 151, and may be a case of being switched and displayed. The following setting such as selection of an anonymization target by the user in the UI image 151 can be performed for each video output destination that outputs the anonymized video generated by the anonymization processing based on the setting. The UI image 151 can be switched to a UI image corresponding to each video output destination by a predetermined operation of the user. FIG. 11 illustrates that three UI images 151 are superimposed and displayed, and the UI images 151 can be switched corresponding to three video output destinations. The video output destination represents, for example, each of the plurality of video display units 101-1 to 101-M included in the information presentation system 14 in FIG. 7. In this case, the anonymized video obtained by anonymizing different anonymization targets can be supplied from the video server 13 to each of the video display units 101-1 to 101-M and displayed.

In the anonymization candidate display unit 161, a video 21 of the camera 41-n and a candidate frame indicating an image region (image range) of the anonymization candidate are drawn. Note that FIG. 11 illustrates a case where the candidate frame indicating the image region is drawn with a line type (line type such as solid line and broken line) corresponding to the identification information (role of person, instrument information specifying an instrument, and the like) of the anonymization candidate. The candidate frame is not limited thereto, and may be drawn in a different drawing form (color or the like) corresponding to each piece of identification information of the anonymization candidate. The candidate frame may be a case where the drawing form of the line itself is the same and character information or the like representing identification information of the anonymization candidate is added.

In the anonymization candidate display unit 161, a video of a camera other than the camera 41-n is superimposed on a back side with respect to the video 21 of the camera 41-n. By the user selecting one of these videos, it is possible to select a video for which selection of an anonymization target or the like is performed (a video on which anonymization processing is performed). The video on which the anonymization processing is performed is a video (output video) that is a source of the anonymized video to be output to the information presentation system 14, and the anonymization candidate display unit 161 also acts as an output video selection unit that selects the output video. Note that the method of selecting the video (output video) on which the anonymization processing is performed is not limited thereto.

In the anonymization selection unit 162, a list of identification information (candidate list) of anonymization candidates included in the video 21 of the camera 41-n and check boxes corresponding to the respective pieces of identification information are drawn. As the identification information of the anonymization candidates, names for identifying the anonymization candidates are used. For example, in a case where the anonymization candidate is a person, a name indicating a role of the person is used as the identification information of the anonymization candidate, and in a case where the anonymization candidate is an instrument, a classification name (a display or the like) indicating a function of the instrument or a character string such as an instrument name or a company name written on the instrument is used as the identification information of the anonymization candidate. Note that, in a case where the anonymization candidate is an instrument, information indicating whether the instrument is a display or another instrument may be used as the identification information of the anonymization candidate, or a figure (image) such as a logo mark written on the instrument may be used as the identification information of the anonymization candidate.

In the anonymization selection unit 162 of FIG. 11, character strings of a nurse, a doctor, an anesthesiologist, a display, and instrument information are drawn as a list of identification information of anonymization candidates. Note that the character string of the instrument information may be a character string or a figure such as a company name specifically written on the instrument.

In the anonymization selection unit 162, the square check box drawn corresponding to the identification information of each anonymization candidate is drawn in the same drawing form (line type) as the candidate frame drawn corresponding to the identification information of each anonymization candidate in the anonymization candidate display unit 161. As a result, the user can recognize, in the anonymization candidate display unit 161, the identification information (the role or the like of the person who is the anonymization candidate) of the anonymization candidate surrounded by the candidate frame.

The user can select whether or not to check a check box corresponding to identification information of each anonymization candidate of the anonymization selection unit 162, and can select the anonymization candidate corresponding to the checked check box as an anonymization target to be actually anonymized. A check mark is drawn in the checked check box, and a check mark is not drawn in a check box that is not checked (is unchecked). The UI unit 81 of the video server 13 determines the anonymization candidate whose check box is checked as an anonymization target. In the anonymization selection unit 162 of FIG. 11, all the check boxes are checked, and a case is illustrated in which all the nurse, doctor, anesthesiologist, display, and instrument information, which are anonymization candidates included in the video 21 of the anonymization candidate display unit 161, are selected and determined as anonymization targets. Note that, in the anonymization selection unit 162, a list of identification information of the anonymization candidates that can be anonymization targets regardless of the video 21 of the camera 41-*n*, and check boxes for selecting whether or not each of the anonymization candidates is to be an anonymization target may be drawn. In that case, the user may determine (limit) the anonymization target (identification information to be anonymized) in advance before the processing of detecting the anonymization candidates included in the video 21 is performed.

In the anonymization result display unit 163, an anonymized video 31 obtained by anonymizing the anonymization targets selected and determined by the anonymization selection unit 162 and a processing frame indicating an image region anonymized for each anonymization target are drawn. The anonymized video 31 is generated by anonymization processing of the image processing unit 82 of the video server 13. In a case where the anonymization target is a person, an image region including the head is anonymized (blurred) by the anonymization processing. However, the image region where the anonymization processing is performed on the person to be anonymized is not limited to the head, and may be an image region of a portion where the skin is exposed or an image region of another portion such as an arm or a hand. In a case where the anonymization target is a display, an image region including the entire screen (for example, the entire display) is anonymized, and the display (screen) is anonymized (blurred). In a case where the anonymization target is an instrument other than the display, an image region including a portion where identification information (instrument name or the like) is written is anonymized (blurred) by the anonymization processing.

In the anonymization result display unit 163, the processing frame for each anonymization target drawn superimposed on the anonymized video 31 is drawn in the same drawing form (line type or the like) as the candidate frame drawn corresponding to the identification information of each anonymization target in the anonymization candidate display unit 161.

The user can visually recognize the anonymized video 31 drawn on the anonymization result display unit 163 and confirm whether or not the anonymization for the video 21 of the camera 41-*n* is appropriate.

In the anonymized video 31, a list of face images of image regions recognized as faces and check boxes corresponding to the respective image regions are drawn in the face detection unit 164.

The list of face images is displayed in a case where an image region recognized as a face is detected as a result of the face recognition processing executed by the face recognition unit 83 of the video server 13 on the anonymized video 31 anonymized by the image processing unit 82.

FIG. 11 illustrates, for example, a case where only the face of the anesthesiologist in the upper left shown in the video 21 of the anonymization candidate display unit 161 is recognized as a face by the face recognition unit 83 and is drawn as a list of face images of the face detection unit 164.

The user visually recognizes the list of face images of the face detection unit 164, and checks the check box corresponding to the face image for which anonymization has been determined to be insufficient. Uncheck (do not check) the check box corresponding to the facial image for which anonymization is determined to be sufficient. In a case where the check box of any of the face images of the face detection unit 164 is checked by the user, the image processing unit 82 of the video server 13 executes additional anonymization processing on the image region of the face image of the anonymized video 31 checked, and generates an anonymized video in which the image region is further blurred. The anonymized video generated by the additional anonymization processing is drawn on the anonymization result display unit 163 as a new anonymized video 31, and the face recognition processing is performed.

Figure 12:
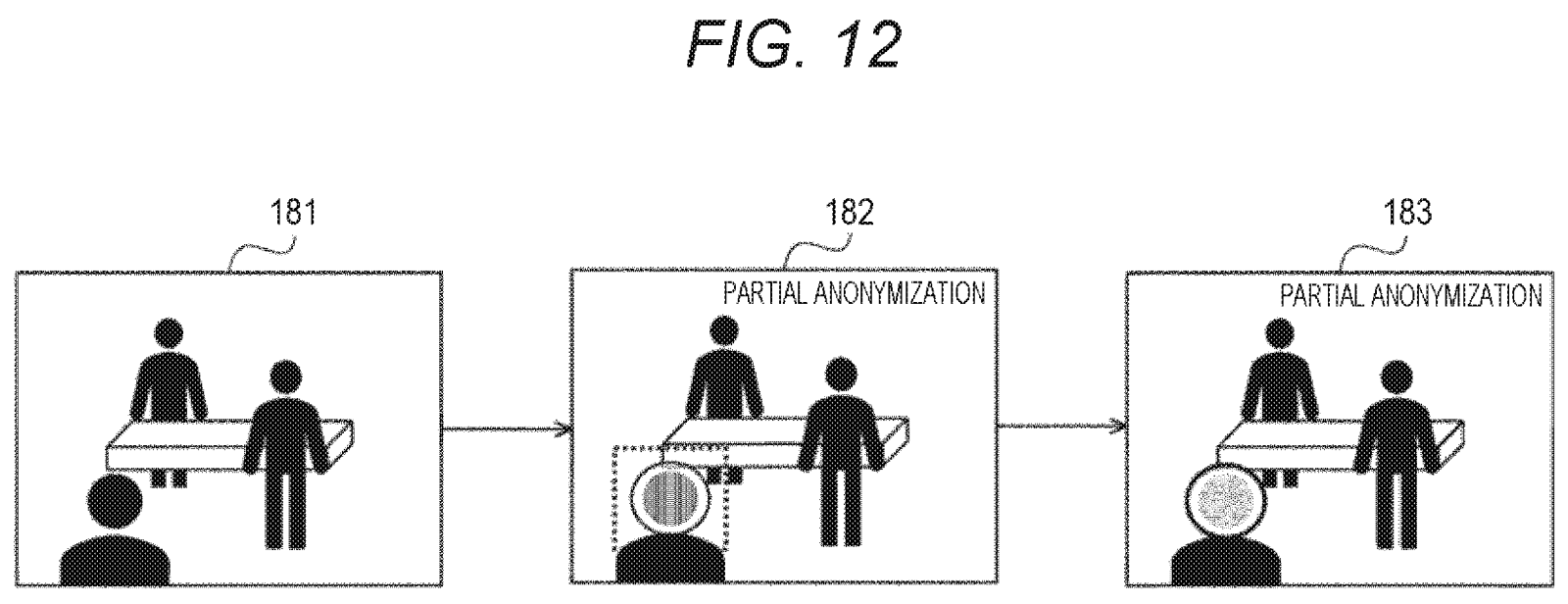

FIG. 12 is a diagram for explaining the additional anonymization processing. In FIG. 12, a video 181 represents a video example of the camera 41-*n* on which the anonymization processing has not been performed. It is assumed that the anonymization processing is performed on an image region of an anonymization target selected by the anonymization selection unit 162 of FIG. 11 for the video 181, and as a result, an anonymized video 182 is generated. The anonymized video 182 shows a case where the anonymization processing is performed on the image region of a square frame including the head of a person at the lower left, and the image region of the head of the person at the lower left is blurred as compared with the video 181. It is assumed that, as a result of executing the face recognition processing on the anonymized video 182, a face image of the person at the lower left is detected in an image region surrounded by a circle frame. At this time, the face image of the person at the lower left is drawn in a list of face images in the face detection unit 164 of FIG. 11. When the user checks a check box corresponding to the face image of the person at the lower left in the list of the face images of the face detection unit 164, the additional anonymization processing for the face image of the person at the lower left is selected. When the additional anonymization processing for the face image of the person at the lower left is selected, the additional anonymization processing is executed for the image region including the face image of the person at the lower left in the anonymized video 182, and an anonymized video 183 is generated. In the anonymized video 183, the face image surrounded by the circle frame of the lower left person is further blurred.

In FIG. 11, when an anonymized video is newly generated by the additional anonymization processing, the anonymized video 31 is drawn in the anonymization result display unit 163, and the face recognition processing is executed. In a case where an image region recognized as a face by the face recognition processing is detected for the new anonymized video 31, a list of face images of the image regions and check boxes corresponding to the respective face images are displayed on the face detection unit 164. In a case where the check box is checked by the user, the additional anonymization processing is further executed. The additional anonymization processing and the face recognition processing are repeatedly executed until the user does not check the check box of any face image in the list of face images of the face detection unit 164 or until no image region recognized as a face is detected.

When the user ends the operation such as the selection of the anonymization target in the UI image 151 of FIG. 11, the finally generated anonymized video 31 is stored in the storage unit (not illustrated) of the video server 13. Note that the anonymized video 31 drawn on the anonymization result display unit 163 may be a case of displaying a result of performing the anonymization processing only on an image of a predetermined frame in the video 21 of the camera 41-$n$. In this case, after the user's operation on the UI image 151 is completed, the image processing unit 82 of the video server 13 generates an anonymized video on the basis of the anonymization target selected (designated) by the user on the UI image 151, the presence or absence of the additional anonymization processing, and the like, and stores the anonymized video in the storage unit of the video server 13.

According to the UI image 151 of the first embodiment described above, the user can simply and freely select the anonymization target to be anonymized according to the output destinations of the video. Therefore, the user can easily select (designate) the anonymization target according to the presentation situation (use) of the video at the output destination of the video, and an appropriate anonymized video according to the presentation situation is generated.

<Second Embodiment of UI Image>

Figure 13:
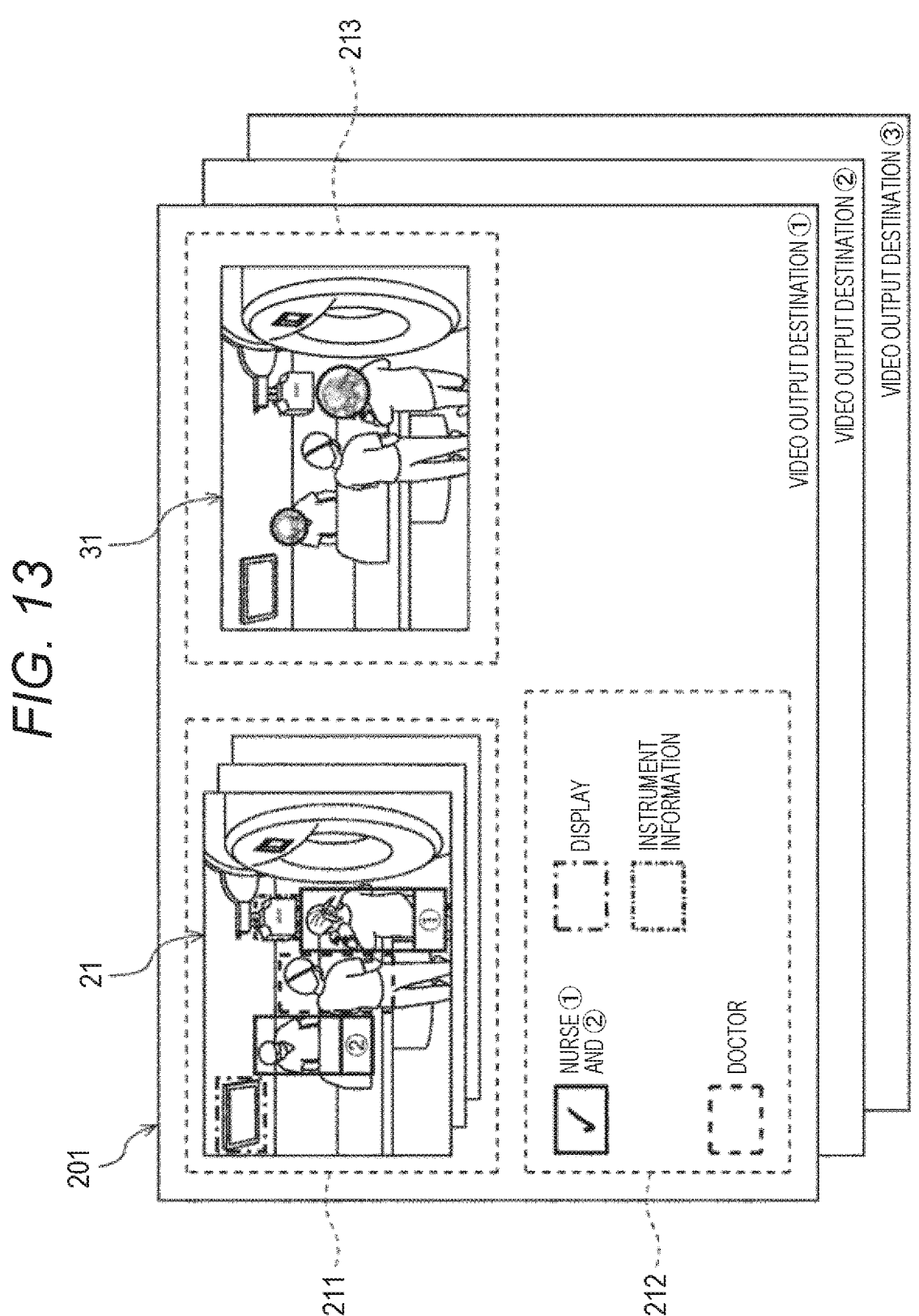
FIG. 13 is a diagram illustrating a configuration example of a second embodiment of a UI image.

FIG. 13 is a diagram illustrating a configuration example of a second embodiment of a UI image generated by the UI unit 81 of the video server 13.

In FIG. 13, a UI image 201 according to the second embodiment is different from the UI image 151 according to the first embodiment in FIG. 11 only in a portion to be described below, and thus description of a portion common to the UI image 151 in FIG. 11 is omitted.

In FIG. 13, the UI image 201 includes an anonymization candidate display unit 211, an anonymization selection unit 212, and an anonymization result display unit 213. The anonymization candidate display unit 211, the anonymization selection unit 212, and the anonymization result display unit 213 correspond to the anonymization candidate display unit 161, the anonymization selection unit 162, and the anonymization result display unit 163 in the UI image 151 of FIG. 11, respectively. In the UI image 201 of FIG. 13, the face detection unit 164 in the UI image 151 of FIG. 11 is omitted.

In FIG. 13, it is assumed that the video 21 of the camera 41-$n$ drawn on the anonymization candidate display unit 211 includes two nurses, one doctor, one display, and one instrument on which identification information (instrument name and the like) is written as anonymization candidates.

In the anonymization selection unit 212, a list of identification information (candidate list) of the anonymization candidates included in the video 21 of the camera 41-$n$ and check boxes corresponding to the respective pieces of identification information are drawn.

In the anonymization selection unit 162 of FIG. 11, in a case where the identification information of the anonymization candidates is different from each other, a corresponding check box is drawn for each identification information. On the other hand, the anonymization selection unit 212 in FIG. 13 represents an aspect in a case where identification information of a plurality of anonymization candidates is common (identical). In the anonymization selection unit 212 of FIG. 13, anonymization candidates having common identification information are presented in the identification information list as one piece of identification information, and one corresponding check box is drawn. Specifically, in the video 21 of the anonymization candidate display unit 211, there are two persons whose identification information is a nurse as anonymization candidates of the common identification information. These nurses are presented as one piece of identification information as nurses 1 and 2 (Numbers of the nurses 1 and 2 in the drawing are indicated by circled numbers.) in the identification information list of the anonymization selection unit 212, and only one corresponding check box is drawn.

In a case where the user checks one check box corresponding to the nurses 1 and 2, two persons who are nurses are collectively selected as anonymization targets.

According to the UI image 201 of the second embodiment described above, the user can collectively select, among the anonymization candidates, the anonymization candidates having common identification information, for example, a plurality of persons, a plurality of displays, or a plurality of instruments having common roles, as anonymization targets. For example, in a case where there are two nurses during the surgery, the persons are displayed separately in the anonymization candidate display unit 211, but both are displayed as nurses in groups in the anonymization selection unit 212. In actual surgery, a peripheral staff other than the doctor who actually performs the surgery is often replaced during the surgery, and it is also assumed that the nurse is replaced by another person. Therefore, in a case where the anonymization candidate is limited to a specific person, the anonymization processing is not performed when the person is replaced. By selecting an anonymization target for each role, the anonymization processing not limited to a specific person can be performed. In this case, when being selected in units of groups of roles in the anonymization selection unit 212, persons classified into the same role as illustrated in the anonymization result display unit 213 are anonymized at a time. In a case where anonymization of a person other than a nurse is not necessary, for example, in a case where anonymization of a doctor is not necessary at a medical office conference or the like, the anonymization processing can be easily performed.

<Third Embodiment of UI Image>

Figure 14:
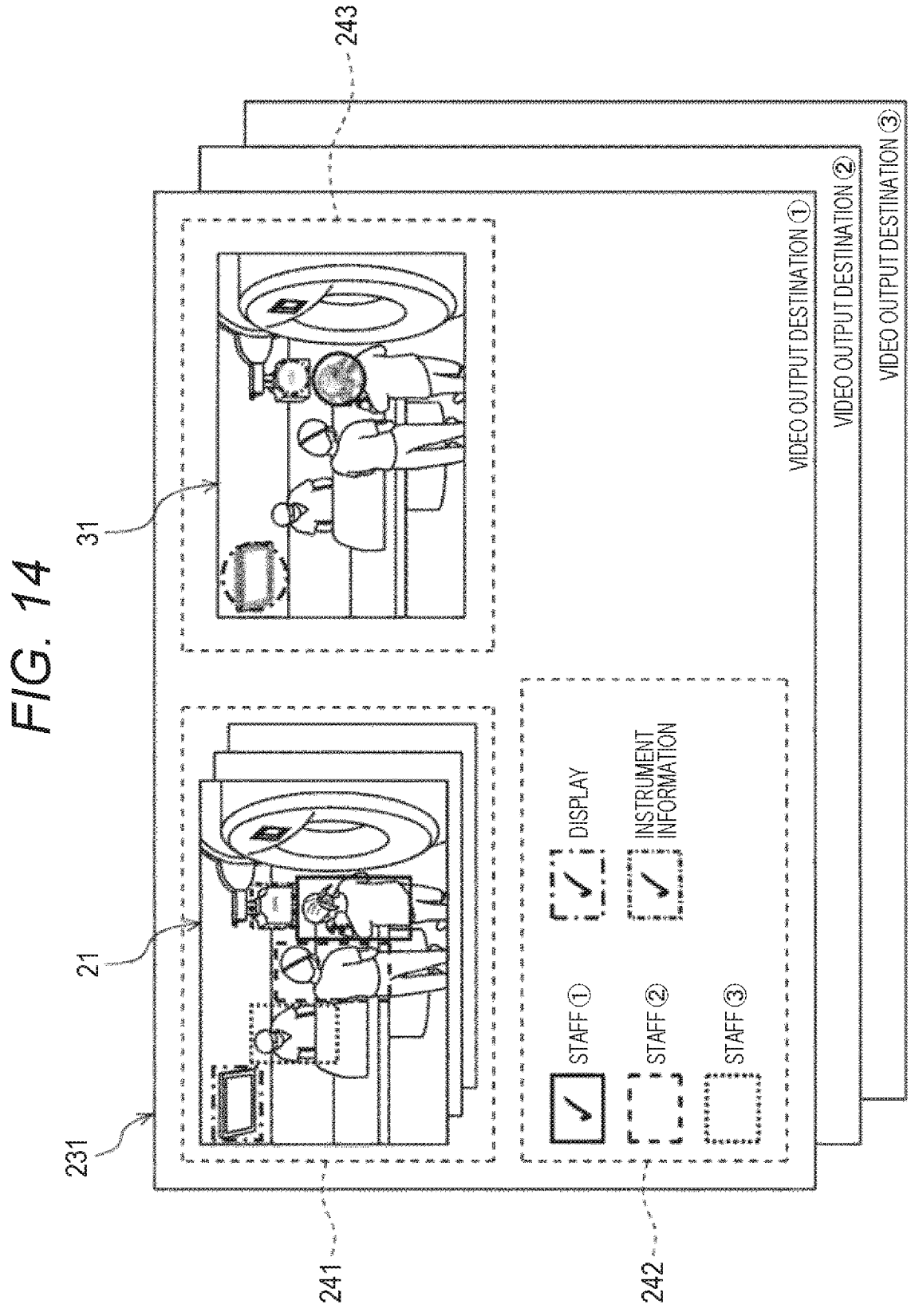
FIG. 14 is a diagram illustrating a configuration example of a third embodiment of a UI image.

FIG. 14 is a diagram illustrating a configuration example of a third embodiment of a UI image generated by the UI unit 81 of the video server 13.

In FIG. 14, a UI image 231 according to the third embodiment is different from the UI image 151 according to the first embodiment in FIG. 11 only in a portion to be described below, and thus description of a portion common to the UI image 151 in FIG. 11 is omitted.

In FIG. 14, the UI image 231 includes an anonymization candidate display unit 241, an anonymization selection unit 242, and an anonymization result display unit 243. The anonymization candidate display unit 241, the anonymization selection unit 242, and the anonymization result display unit 243 correspond to the anonymization candidate display unit 161, the anonymization selection unit 162, and the anonymization result display unit 163 in the UI image 151 of FIG. 11, respectively. In the UI image 201 of FIG. 13, the face detection unit 164 in the UI image 151 of FIG. 11 is omitted.

In FIG. 14, the video 21 of the camera 41-*n* drawn on the anonymization candidate display unit 241 includes three staffs, one display, and one instrument on which identification information (instrument name and the like) is written as anonymization candidates.

In the anonymization selection unit 242, a list of identification information (candidate list) of anonymization candidates included in the video 21 of the camera 41-*n* and check boxes corresponding to the respective pieces of identification information are drawn.

In the anonymization selection unit 162 of FIG. 11, as described above, in a case where the identification information of the anonymization candidates is different from each other, a corresponding check box is drawn for each identification information. On the other hand, the anonymization selection unit 242 in FIG. 14 represents an aspect in a case where identification information of a plurality of anonymization candidates is common (identical).

In the anonymization selection unit 242 of FIG. 14, anonymization candidates having common identification information are also presented in the identification information list as individual identification information, and one check box corresponding to each is drawn. Specifically, in the video 21 of the anonymization candidate display unit 241, there are three persons whose identification information is a staff as anonymization candidates of the common identification information. In the identification information list of the anonymization selection unit 242, those staffs are presented as different identification information as staffs 1, 2, and 3 (the number portion in the figure is indicated by a circled number), and only check box is drawn in each of the staffs.

When the user selects whether or not to check the check box corresponding to each of the staffs 1, 2, and 3, the three persons who are the staffs are individually selected as anonymization targets.

According to the UI image 231 of the third embodiment described above, the user can individually select, from among the anonymization candidates, an anonymization candidate having common identification information, for example, a plurality of persons, a plurality of displays, or a plurality of instruments having common roles, as an anonymization target.

For example, it is not necessary to anonymize the staff when utilizing the surgical video individually mainly from an educational viewpoint for the individual staff, such as post-review of the intraoperative workflow. In this case, only the other staff can be anonymized individually.

<Fourth Embodiment of UI Image>

Figure 15:
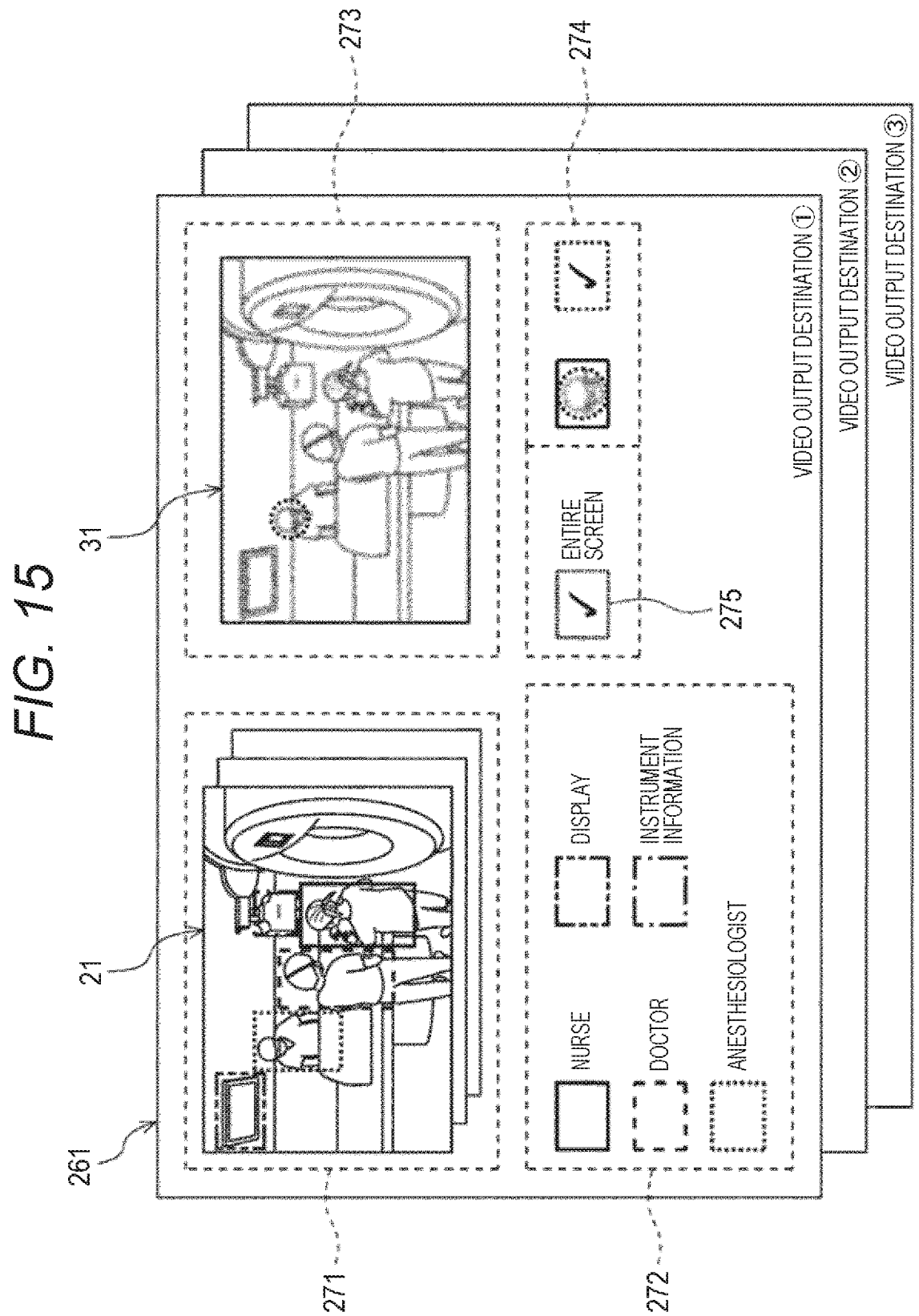
FIG. 15 is a diagram illustrating a configuration example of a fourth embodiment of a UI image.

FIG. 15 is a diagram illustrating a configuration example of a fourth embodiment of a UI image generated by the UI unit 81 of the video server 13.

In FIG. 15, a UI image 261 according to the fourth embodiment is different from the UI image 151 according to the first embodiment in FIG. 11 only in a portion to be described below, and thus description of a portion common to the UI image 151 in FIG. 11 is omitted.

In FIG. 15, the UI image 261 includes an anonymization candidate display unit 271, an anonymization selection unit 272, an anonymization result display unit 273, a face detection unit 274, and an entire anonymization selection unit 275. The anonymization candidate display unit 271, the anonymization selection unit 272, the anonymization result display unit 273, and the face detection unit 274 correspond to the anonymization candidate display unit 161, the anonymization selection unit 162, the anonymization result display unit 163, and the face detection unit 164 in the UI image 151 of FIG. 11, respectively. The UI image 201 of FIG. 13 is different from the UI image 151 of FIG. 11 in newly including the entire anonymization selection unit 275.

A check box is drawn in the entire anonymization selection unit 275 in FIG. 15. When the user checks this check box, the anonymization processing is performed on the entire image region of the video 21 of the camera 41-*n*, and the anonymized video 31 in which the entire video 21 is blurred is generated.

As a result of performing the face recognition processing on the anonymized video 31 subjected to the anonymization processing, when an image region of a face image recognized as a face is detected, the face image detected by the face detection unit 274 and a check box are drawn. When the user checks the check box of the face detection unit 274, the additional anonymization processing is performed on the image region of the face image.

Figure 16:
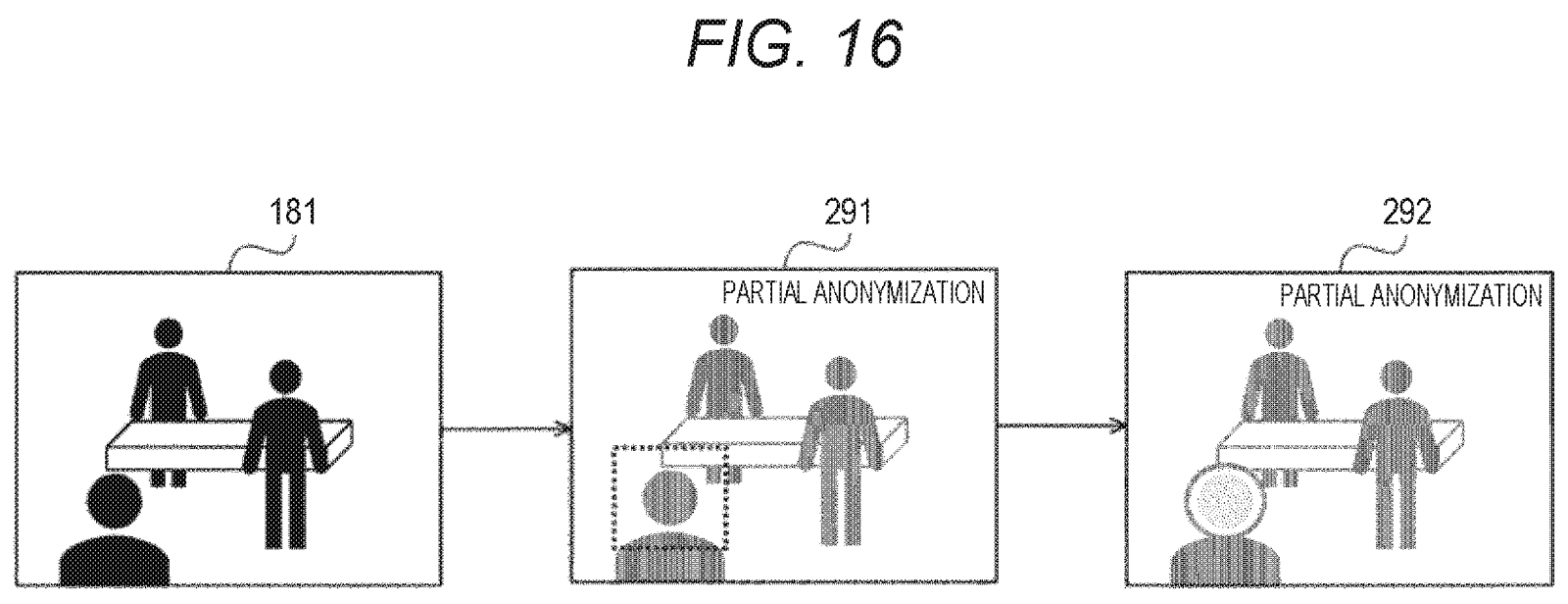

FIG. 16 is a diagram illustrating the additional anonymization processing after an entire video is anonymized. In FIG. 16, a video 181 represents a video example of the camera 41-*n* that is not anonymized. It is assumed that the anonymization processing is performed on an entire image region of the video 181 by the selection of the entire anonymization selection unit 275 in FIG. 15, and as a result, an anonymized video 291 is generated. The entire image region of the anonymized video 291 is blurred compared to the video 181. It is assumed that, as a result of executing the face recognition processing on the anonymized video 291, a face image of a person at the lower left is detected in an image region surrounded by a circle frame. At this time, the face image of the person at the lower left is drawn in a list of face images in the face detection unit 274 of FIG. 15. When the user checks the check box corresponding to the face image of the person at the lower left in the list of the face images of the face detection unit 274 and selects the additional anonymization processing, the additional anonymization processing is executed on the image region including the face image of the person at the lower left in the anonymized video 291, and an anonymized video 292 is generated. In the anonymized video 292, the face image surrounded by the circle frame of the lower left person is further blurred.

The UI image 261 according to the fourth embodiment described above is useful in a case where anonymization of the entire screen is necessary. For example, in a case where it is necessary to conceal not only personal information of a person but also information of a facility, such as television broadcasting, partial anonymization is assumed to be insufficient, and thus the entire screen needs to be anonymized.

<Program>

A series of processing or a part of processing in the information processing system 1 described above can be executed by hardware or software. In a case where the series of processing is executed by the software, a program constituting the software is installed on a computer. Here, examples of the computer include a computer incorporated in dedicated hardware, and a general-purpose personal computer capable of executing various functions by installing various programs, for example.

Figure 17:
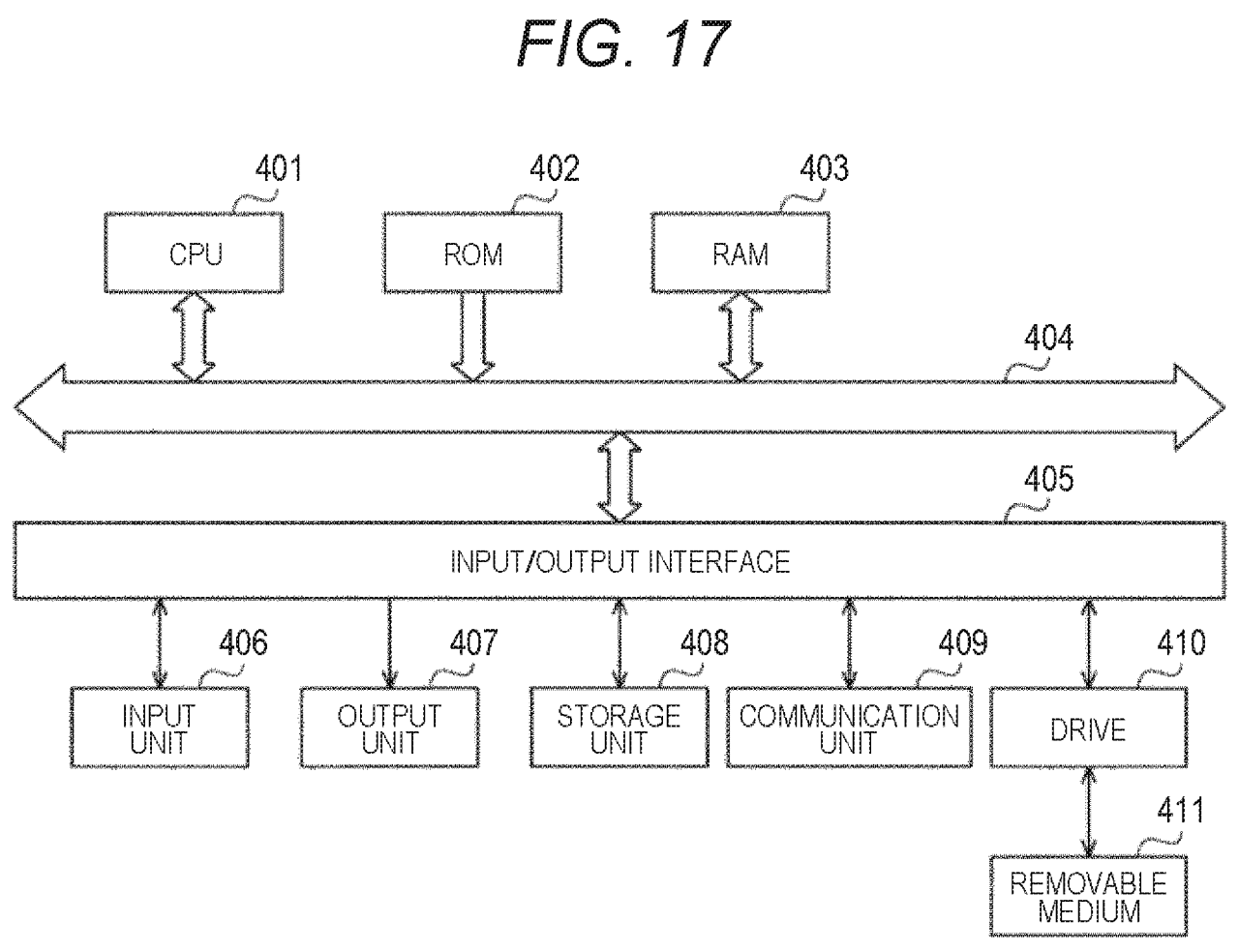

FIG. 17 is a block diagram illustrating a configuration example of hardware of a computer in a case where the computer executes each processing executed by the information processing system 1 by a program.

In the computer, a central processing unit (CPU) 401, a read only memory (ROM) 402, and a random access memory (RAM) 403 are mutually connected by a bus 404.

An input/output interface 405 is further connected to the bus 404. An input unit 406, an output unit 407, a storage unit 408, a communication unit 409, and a drive 410 are connected to the input/output interface 405.

The input unit 406 includes a keyboard, a mouse, a microphone, and the like. The output unit 407 includes a display, a speaker, and the like. The storage unit 408 includes a hard disk, a nonvolatile memory, and the like. The communication unit 409 includes a network interface and the like. The drive 410 drives a removable medium 411 such as a magnetic disk, an optical disk, a magneto-optical disk, a semiconductor memory, or the like.

In the computer configured as described above, for example, the CPU 401 loads a program stored in the storage unit 408 into the RAM 403 via the input/output interface 405 and the bus 404 and executes the program, so that the above-described series of processing is performed.

The program executed by the computer (CPU 401) can be provided by being recorded in the removable medium 411 as a package medium or the like, for example. Furthermore, the program can be provided via a wired or wireless transmission medium such as a local area network, the Internet, or digital broadcasting.

In the computer, the program can be installed in the storage unit 408 via the input/output interface 405 by attaching the removable medium 411 to the drive 410. Furthermore, the program can be received by the communication unit 409 via a wired or wireless transmission medium and installed in the storage unit 408. In addition, the program can be installed in the ROM 402 or the storage unit 408 in advance.

Note that the program executed by the computer may be a program that performs processing in a time-series manner in the order described in the present specification, or may be a program that performs processing in parallel or at necessary timing such as when a call is made.

Application Example

The technology according to the present disclosure can be applied to various products. For example, the present technology may be applied to an operating room system.

Figure 18:
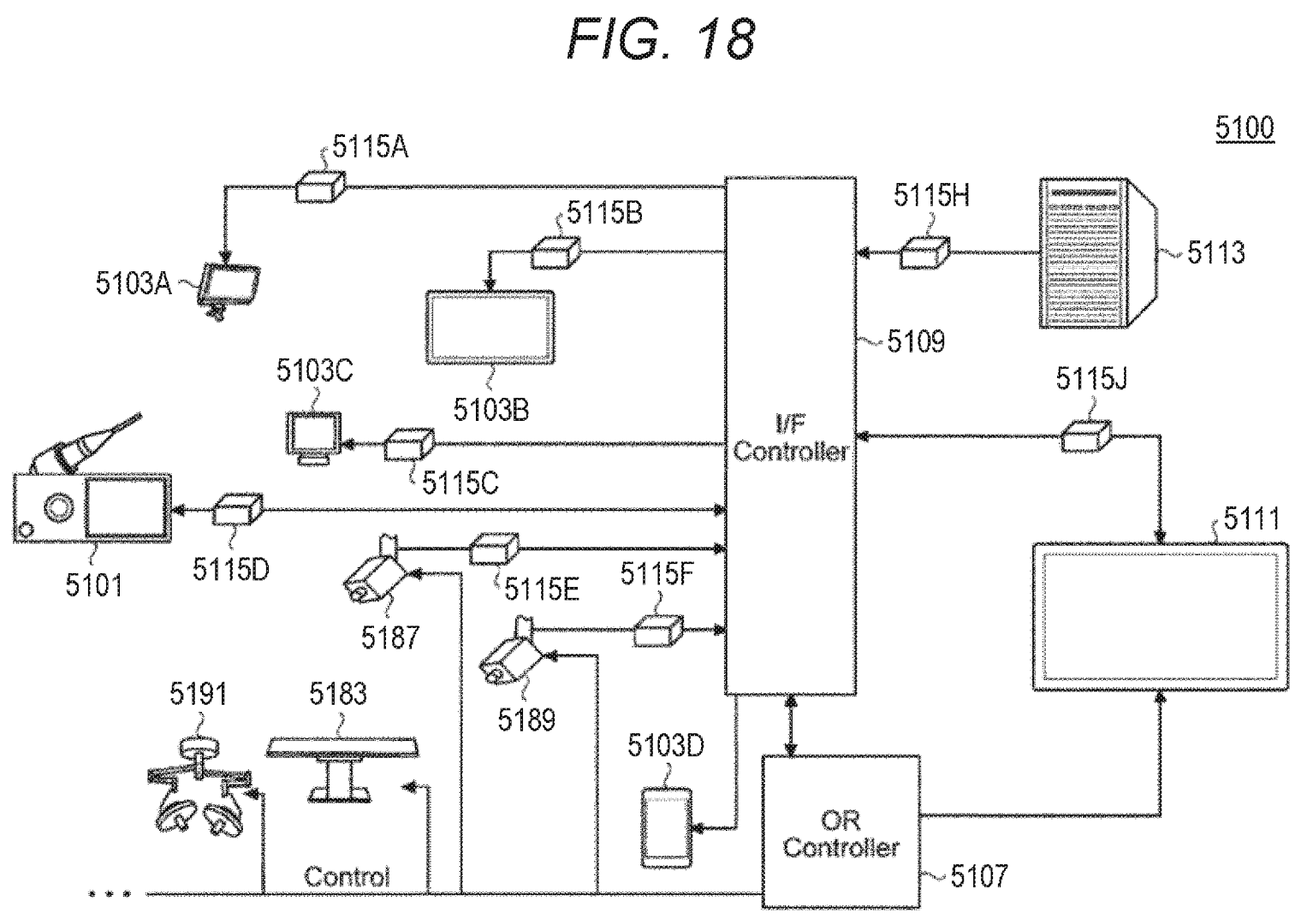

FIG. 18 is a diagram schematically illustrating an overall configuration of an operating room system 5100 to which the technology according to the present disclosure can be applied. Referring to FIG. 18, the operating room system 5100 is configured by connecting a device group installed in an operating room to be able to cooperate with each other via an operating room controller (OR Controller) 5107 and an input/output controller (I/F Controller) 5109. The operating room system 5100 is configured using an Internet Protocol (IP) network capable of transmitting and receiving 4K/8K images, and transmits and receives input and output images and control information for the devices via the IP network.

Various devices can be installed in the operating room. FIG. 18 illustrates, as an example, a group of various devices 5101 for endoscopic surgery, a ceiling camera 5187 that is provided on the ceiling of the operating room and captures an image of the hands of an operator, an operating field camera 5189 that is provided on the ceiling of the operating room and captures an image of the entire operating room, a plurality of display devices 5103A to 5103D, a patient bed 5183, and a light 5191. In addition to an endoscope illustrated in FIG. B1, various medical devices for acquiring images and videos, such as a master-slave endoscopic surgery robot and an X-ray imaging device, may be applied to the group of devices 5101.

The group of devices 5101, the ceiling camera 5187, the operating field camera 5189, and the display devices 5103A to 5103C are connected to the IF controller 5109 via IP converters 5115A to 5115F (hereinafter, denoted by reference numeral 5115 when not individually distinguished). The IP converters 5115D, 5115E, and 5115F on video source sides (camera sides) perform IP conversion on videos from individual medical image capturing devices (such as an endoscope, an operation microscope, an X-ray imaging device, an operating field camera, and a pathological image capturing device), and transmit the results on the network. The IP converters 5115A to 5115D on video output sides (monitor sides) convert the videos transmitted through the network into monitor-unique formats, and output the results. The IP converters on the video source sides function as encoders, and the IP converters on the video output sides function as decoders. The IP converters 5115 may have various image processing functions, and may have functions of, for example, resolution conversion processing corresponding to output destinations, rotation correction and image stabilization of an endoscopic video, and object recognition processing. The image processing functions may also include partial processing such as feature information extraction for analysis on a server described later.

These image processing functions may be specific to the connected medical image devices, or may be upgradable from outside. The IP converters on the display sides can perform processing such as synthesis of a plurality of videos (for example, picture-in-picture (PinP) processing) and superimposition of annotation information. The protocol conversion function of each of the IP converters is a function to convert a received signal into a converted signal conforming to a communication protocol allowing the signal to be transmitted on the network (such as the Internet). Any communication protocol may be set as the communication protocol. The signal received by the IP converter and convertible in terms of protocol is a digital signal, and is, for example, a video signal or a pixel signal. The IP converter may be incorporated in a video source side device or in a video output side device.

The group of devices 5101 belong to, for example, an endoscopic surgery system, and include, for example, the endoscope and a display device for displaying an image captured by the endoscope. The display devices 5103A to 5103D, the patient bed 5183, and the light 5191 are, for example, devices equipped in the operating room separately from the endoscopic surgery system. Each of these devices for surgical or diagnostic is also called a medical device. The OR controller 5107 and/or the IF controller 5109 controls operations of the medical devices in cooperation. When the endoscopic surgery robot (surgery master-slave) system and the medical image acquisition devices such as an X-ray imaging device are included in the operating room, those devices can also be connected as the group of devices 5101 in the same manner.

The OR controller 5107 controls processing related to image display in the medical devices in an integrated manner. Specifically, the group of devices 5101, the ceiling camera 5187, and the operating field camera 5189 among the devices included in the operating room system 5100 can each be a device having a function to transmit (hereinafter, also called a transmission source device) information to be displayed (hereinafter, also called display information) during the operation. The display devices 5103A to 5103D can each be a device to output the display information (hereinafter, also called an output destination device). The OR controller 5107 has a function to control operations of the transmission source devices and the output destination devices so as to acquire the display information from the transmission source devices and transmit the display information to the output destination devices to cause the output destination devices to display or record the display information. The display information refers to, for example, various images captured during the operation and various types of information on the operation (for example, body information and past examination results of a patient and information about a surgical procedure).

Specifically, information about an image of a surgical site in a body cavity of the patient captured by the endoscope can be transmitted as the display information from the group of devices 5101 to the OR controller 5107.

Information about an image of the area near the hands of the operator captured by the ceiling camera 5187 can be transmitted as the display information from the ceiling camera 5187. Information about an image representing the overall situation in the operating room captured by the operating field camera 5189 can be transmitted as the display information from the operating field camera 5189. When another device having an imaging function is present in the operating room system 5100, the OR controller 5107 may also acquire information about an image captured by the other device as the display information from the other device.

The OR controller 5107 displays the acquired display information (that is, the images captured during the operation and the various types of information on the operation) on at least one of the display devices 5103A to 5103D serving as the output destination devices. In the illustrated example, the display device 5103A is a display device installed on the ceiling of the operating room, being hung therefrom; the display device 5103B is a display device installed on a wall surface of the operating room; the display device 5103C is a display device installed on a desk in the operating room; and the display device 5103D is a mobile device (such as a tablet personal computer (PC)) having a display function.

The IF controller 5109 controls input and output of the video signal from and to connected devices. For example, the IF controller 5109 controls input and output of the video signal based on controlling of the OR controller 5107. The IF controller 5109 includes, for example, an IP switcher, and controls high-speed transfer of the image (video) signal between devices disposed on the IP network.

The operating room system 5100 may include a device outside the operating room. The device outside the operating room can be a server connected to a network built in and outside a hospital, a PC used by a medical staff, or a projector installed in a meeting room of the hospital. When such an external device is present outside the hospital, the OR controller 5107 can also display the display information on a display device of another hospital via, for example, a teleconference system for telemedicine.

An external server 5113 is, for example, an in-hospital server or a cloud server outside the operating room, and may be used for, for example, image analysis and/or data analysis. In this case, the video information in the operating room may be transmitted to the external server 5113, and the server may generate additional information through big data analysis or recognition/analysis processing using artificial intelligence (AI) (machine learning), and feed the additional information back to the display devices in the operating room. At this time, an IP converter 5115H connected to the video devices in the operating room transmits data to the external server 5113, so that the video is analyzed. The transmitted data may be, for example, a video itself of the operation using the endoscope or other tools, metadata extracted from the video, and/or data indicating an operating status of the connected devices.

The operating room system 5100 is further provided with a central operation panel 5111. Through the central operation panel 5111, a user can give the OR controller 5107 an instruction about input/output control of the IF controller 5109 and an instruction about an operation of the connected devices. Furthermore, the user can switch image display via the central operation panel 5111. The central operation panel 5111 is configured by providing a touchscreen on a display surface of a display device. The central operation panel 5111 may be connected to the IF controller 5109 via an IP converter 5115J.

The IP network may be established using a wired network, or a part or the whole of the network may be established using a wireless network. For example, each of the IP converters on the video source sides may have a wireless communication function, and may transmit the received image to an output side IP converter via a wireless communication network, such as the fifth-generation mobile communication system (5G) or the sixth-generation mobile communication system (6G).

The technology according to the present disclosure can be applied to the group of devices 5101, the display devices 5103A to 5103D, the OR controller 5107, the IF controller 5109, the central operation panel 5111, the external server 5113, the IP converter 5115, the ceiling camera 5187, the operating field camera 5189, and devices outside the operating room among the above-described configurations. Specifically, the data collection device 11 in the information processing system 1 of FIG. 1 to which the technology according to the present disclosure is applied is applied to a medical image acquisition device of the group of devices 5101, the ceiling camera 5187, and the operating field camera 5189 to collect the video. The person information detection processing and the instrument appearance information detection processing in the data processing device 12 in the information processing system 1 in FIG. 1, and the processing of the determination of the anonymization target and the generation of the anonymized video in the video server 13 are executed in any one device among the OR controller 5107, the IF controller 5109, the central operation panel 5111, the external server 5113, the IP converter 5115, and devices outside the operating room, or are executed in a distributed manner in any plurality of devices among these devices to generate the anonymized video. The information presentation system 14 in the information processing system 1 of FIG. 1 is applied to the display device of the group of devices 5101, the display devices 5103A to 5103D, the central operation panel 5111, and a display device as a device outside the operating room to present the anonymized video. As a result, it is possible to determine an appropriate anonymization target and generate an appropriate anonymized video according to the display device that displays or the situation of displaying the video acquired by each of the medical image acquisition device of the group of devices 5101, the ceiling camera 5187, and the operating field camera 5189.

The present technology can also have the following configurations.

(1)

An information processing system including:

an image recognition unit that detects anonymization candidates that can be an anonymization target included in a target image captured in a medical facility;

an anonymization target determination unit that determines an anonymization target in the target image on the basis of an operation of a user; and an image processing unit that generates, for the target image, an anonymized image obtained by anonymizing an image region of the anonymization target determined by the anonymization target determination unit among the anonymization candidates detected by the image recognition unit.

(2)

The information processing system according to (1) described above, in which the image recognition unit detects a person, a display, or an object on which identification information is written as the anonymization candidates.

(3)

The information processing system according to (1) or (2) described above, in which the image recognition unit detects a person as the anonymization candidates, and estimates and detects a role of the person as identification information of the person.

(4)

The information processing system according to (3) described above, in which the anonymization target determination unit determines the person to be the anonymization target on the basis of identification information of the person.

(5)

The information processing system according to any one of (1) to (4) described above, in which the anonymization target determination unit generates an input image to be presented to the user to select the anonymization target.

(6)

The information processing system according to (5) described above, in which the anonymization target determination unit presents, in the input image, the anonymization candidates detected by the image recognition unit, and presents a selection unit that allows the user to select whether or not to determine the presented anonymization candidates as the anonymization target.

(7)

The information processing system according to (6) described above, in which the image recognition unit detects a person as the anonymization candidates and estimates a role of the person as identification information of the person, and the anonymization target determination unit presents the selection unit that allows the user to select whether or not to determine for each piece of the identification information of the anonymization candidates as the anonymization target.

(8)

The information processing system according to (6) described above, in which the image recognition unit detects a person as the anonymization candidates and estimates a role of the person as identification information of the person, and the anonymization target determination unit presents the selection unit that allows the user to select whether or not to determine for each of the anonymization candidates as the anonymization target.

(9)

The information processing system according to any one of (6) to (8) described above, in which the anonymization target determination unit presents, in the input image, the anonymized image obtained by anonymizing the image region of the anonymization target determined by selection in the selection unit.

(10)

The information processing system according to (9) described above, further including a face recognition unit that detects a face image recognized as a face with respect to the anonymized image, in which the anonymization target determination unit presents the face image detected by the face recognition unit in the input image, and presents a face detection unit that allows the user to select whether or not to perform additional anonymization on the face image.

(11)

The information processing system according to any one of (6) to (10) described above, in which the anonymization target determination unit presents an entire anonymization selection unit that allows the user to select whether or not to anonymize entirety of the target image in the input image.

(12)

The information processing system according to any one of (1) to (11) described above, in which the anonymization target determination unit determines the anonymization target for each of output destinations of the anonymized image.

(13)

The information processing system according to any one of (5) to (12) described above, in which the image recognition unit detects an instrument in which a company name or an instrument name is written as the anonymization candidates, and sets the company name or the instrument name as identification information of the instrument.

(14)

The information processing system according to any one of (1) to (13) described above, in which the image processing unit generates, for the target image, the anonymized image by performing mosaic processing or blurring processing of the image region of the anonymization target.

(15)

An information processing method in an information processing system including:

an image recognition unit;

an anonymization target determination unit; and an image processing unit, the information processing method including:

detecting, by the image recognition unit, anonymization candidates that can be an anonymization target included in a target image captured in a medical facility;

determining, by the anonymization target determination unit, an anonymization target in the target image on the basis of an operation of a user; and for the target image, generating, by the image processing unit, an anonymized image obtained by anonymizing an image region of the anonymization target determined by the anonymization target determination unit among the anonymization candidates detected by the image recognition unit.

(16)

A program for causing a computer to function as:

an image recognition unit that detects anonymization candidates that can be an anonymization target included in a target image captured in a medical facility;

an anonymization target determination unit that determines an anonymization target in the target image on the basis of an operation of a user; and an image processing unit that generates, for the target image, an anonymized image obtained by anonymizing an image region of the anonymization target determined by the anonymization target determination unit among the anonymization candidates detected by the image recognition unit.

REFERENCE SIGNS LIST

1 Information processing system
11 Data collection device
12 Data processing device
13 Video server
14 Information presentation system
41-1 to 41-N Camera
51 Image recognition unit
52 Data generation unit
61 Person posture recognition unit
62 Role estimation unit
63 Object recognition unit
81 UI unit
82 Image processing unit
83 Face recognition unit
101-1 to 101-M Video display unit
151 UI image
161 Anonymization candidate display unit
162 Anonymization selection unit
163 Anonymization result display unit
164 Face detection unit

The invention claimed is:

1. An information processing system, comprising:

an image recognition unit configured to detect a plurality of anonymization candidates included in a target image captured in a medical facility;

an anonymization target determination unit configured to determine, based on an operation of a user, an anonymization target of the plurality of anonymization candidates in the target image;

an image processing unit configured to generate, for the target image, an anonymized image obtained by an anonymizing operation on an image region of the determined anonymization target; and a face recognition unit configured to detect a face image from the generated anonymized image, wherein the face image comprises an image of a face of the determined anonymization target, the image processing unit is further configured to perform an additional anonymization operation on the image region of the determined anonymization target based on the detected face image, and the anonymization target determination unit is further configured to:

generate an input image;

present the detected face image in the input image; and present a face detection unit that allows the user to select whether to perform the additional anonymization operation on the image region.

2. The information processing system according to claim 1, wherein the image recognition unit is further configured to detect a person, a display, or an object on which identification information is written as the plurality of anonymization candidates.

3. The information processing system according to claim 1, wherein the image recognition unit is further configured to:

detect a person as an anonymization candidate of the plurality of anonymization candidates; and determine a role of the detected person as identification information of the person.

4. The information processing system according to claim 3, wherein the anonymization target determination unit is further configured to determine the person as the anonymization target based on the identification information of the person.

5. The information processing system according to claim 1, wherein the anonymization target determination unit is further configured to generate the input image to present to the user for selection of the anonymization target.

6. The information processing system according to claim 5, wherein the anonymization target determination unit is further configured to:

present, in the input image, the detected plurality of anonymization candidates; and present a selection unit that allows the user to select whether to determine an anonymization candidate of the presented plurality of anonymization candidates as the anonymization target.

7. The information processing system according to claim 6, wherein the image recognition unit is further configured to:

detect a plurality of persons as the plurality of anonymization candidates; and determine a role of each person of the detected plurality of persons as identification information, the anonymization target determination unit is further configured to present the selection unit that allows the user to select whether or not to determine at least one anonymization candidate, of the plurality of anonymization candidates, for each piece of the identification information as at least one anonymization target, and the at least one anonymization target comprises the anonymization target.

8. The information processing system according to claim 6, wherein the image recognition unit is further configured to:

detect a person as the anonymization candidate of the plurality of anonymization candidates; and determine a role of the person as individual identification information, and the anonymization target determination unit is further configured to present the selection unit that allows the user to select whether to determine, based on the individual identification information, the person as the anonymization target.

9. The information processing system according to claim 6, wherein the anonymization target determination unit is further configured to present, in the input image, the generated anonymized image.

10. The information processing system according to claim 6, wherein the anonymization target determination unit is further configured to present an entire anonymization selection unit that allows the user to select whether to anonymize an entirety of the target image in the input image.

11. The information processing system according to claim 1, wherein the anonymization target determination unit is further configured to determine the anonymization target for each output destination of a plurality of output destinations of the anonymized image.

12. The information processing system according to claim 5, wherein the image recognition unit is configured to:

detect an instrument in which at least one of a company name or an instrument name is written as an anonymization candidate of the plurality of anonymization candidates, and set the at least one of the company name or the instrument name as identification information of the instrument.

13. The information processing system according to claim 1, wherein the image processing unit is further configured to generate, for the target image, the anonymized image by one of a mosaic processing operation or a blurring processing operation of the image region of the anonymization target.

14. An information processing method, comprising:

in an information processing system:

detecting, by an image recognition unit, a plurality of anonymization candidates included in a target image captured in a medical facility;

determining, by an anonymization target determination unit, an anonymization target of the plurality of anonymization candidates in the target image based on an operation of a user;

generating, by an image processing unit, for the target image, an anonymized image obtained by an anonymizing operation on an image region of the determined anonymization target;

detecting, by a face recognition unit, a face image from the generated anonymized image, wherein the face image comprises an image of a face of the determined anonymization target;

performing, by the image processing unit, an additional anonymization operation on the image region of the determined anonymization target based on the detected face image;

generating, by the anonymization target determination unit, an input image;

presenting, by the anonymization target determination unit, the detected face image in the input image; and presenting, by the anonymization target determination unit, a face detection unit that allows the user to select whether to perform the additional anonymization operation on the image region.

15. A non-transitory computer-readable medium having stored thereon, computer-executable instructions which, when executed by a computer, cause the computer to execute operations, the operations comprising:

detecting a plurality of anonymization candidates included in a target image captured in a medical facility;

determining an anonymization target of the plurality of anonymization candidates in the target image based on an operation of a user;

generating, for the target image, an anonymized image obtained by an anonymizing operation on an image region of the determined anonymization target;

detecting a face image from the generated anonymized image, wherein the face image comprises an image of a face of the determined anonymization target;

performing an additional anonymization operation on the image region of the determined anonymization target based on the detected face image;

generating an input image;

presenting the detected face image in the input image; and presenting a face detection unit that allows the user to select whether to perform the additional anonymization operation on the image region.

* * * * *